US011806661B2

(12) United States Patent
Hironaka

(10) Patent No.: US 11,806,661 B2
(45) Date of Patent: Nov. 7, 2023

(54) POLYMER AND METHOD FOR PRODUCING THE SAME, GAS SEPARATION MEMBRANE, GAS SEPARATION MODULE, AND GAS SEPARATION APPARATUS USING THE POLYMER, AND M-PHENYLENEDIAMINE COMPOUND

(71) Applicant: FUJIFILM Corporation, Tokyo (JP)

(72) Inventor: Koji Hironaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 177 days.

(21) Appl. No.: 17/412,244

(22) Filed: Aug. 25, 2021

(65) Prior Publication Data

US 2021/0394113 A1 Dec. 23, 2021

Related U.S. Application Data

(63) Continuation of application No. PCT/JP2020/008324, filed on Feb. 28, 2020.

(30) Foreign Application Priority Data

Feb. 28, 2019 (JP) ................................ 2019-035097
Jul. 23, 2019 (JP) ................................ 2019-135161

(51) Int. Cl.
*B01D 53/22* (2006.01)
*B01D 69/12* (2006.01)
(Continued)

(52) U.S. Cl.
CPC ............ *B01D 53/22* (2013.01); *B01D 69/12* (2013.01); *B01D 71/42* (2013.01); *B01D 71/64* (2013.01); *C07C 211/52* (2013.01); *C08G 73/026* (2013.01)

(58) Field of Classification Search
None
See application file for complete search history.

(56) References Cited

U.S. PATENT DOCUMENTS 6,303,743 B1 10/2001 You et al.
10,040,035 B2 8/2018 Usami et al.
(Continued)

FOREIGN PATENT DOCUMENTS

CN 104447441 3/2015
JP S63235334 9/1988
(Continued)

OTHER PUBLICATIONS

English language machine translation for JP 8-198964. Retrieved from translationportal.epo.org on Apr. 17, 2023. (Year: 2023).*
(Continued)

*Primary Examiner* — Jason M Greene
(74) *Attorney, Agent, or Firm* — JCIPRNET

(57) ABSTRACT

Provided are a polymer having a constituent component represented by formula (I) below, a method for producing the polymer, a diamine compound suitable as a raw material for the polymer, a gas separation membrane haying a gas separation layer including the polymer, and a gas separation module and a gas separation apparatus that have the gas separation membrane.

(Continued)

CO2, CH4
10
1
2
CO2 rich

Formula (I)

$$R^A,\ R^B,\ R^C,\ CF_3$$

In the formula (I), $R^A$, $R^B$, and $R^C$ represent a hydrogen atom, an alkyl group having 1 to 4 carbon atoms, or a halogen atom. Herein, at least one of $R^A$, $R^B$, or $R^C$ represents an alkyl group having 1 to 4 carbon atoms or a halogen atom. The alkyl group having 1 to 4 carbon atoms is not trifluoromethyl and ** represents linking sites.

10 Claims, 1 Drawing Sheet

(51) Int. Cl.

*B01D 71/42* (2006.01)
*B01D 71/64* (2006.01)
*C07C 211/52* (2006.01)
*C08G 73/02* (2006.01)

(56) References Cited

U.S. PATENT DOCUMENTS

2014/0174293 A1 6/2014 Yamanaka et al.
2015/0322100 A1 11/2015 Roeschenthaler et al.
2016/0199790 A1* 7/2016 Usami .................... B01D 71/64 95/51
2016/0214067 A1* 7/2016 Miller .................. B01D 53/228
2016/0271569 A1 9/2016 Hanley et al.

FOREIGN PATENT DOCUMENTS

JP S6465113 3/1989
JP H05112635 5/1993
JP 8-198964 * 8/1996 ............. B01D 71/64
JP H08198964 8/1996
JP 2005047825 2/2005
JP 2015083296 4/2015
JP 2019502765 1/2019
WO 2015129554 9/2015
WO 2016153064 9/2016
WO 2018097142 5/2018

OTHER PUBLICATIONS

Zhu Chun et al., “Fluorine—Containing Polyimide Membrane for Gas Separation” Organo—Fluorine Industry, Jan. 2012, submit with English abstract, pp. 1-5.
“Office Action of China Counterpart Application”, dated Dec. 1, 2022, with English translation thereof, pp. 1-24.
“International Search Report (Form PCT/ISA/210) of PCT/JP2020/008324,” dated May 19, 2020, with English translation thereof, pp. 1-5.
“Written Opinion of the International Searching Authority (Form PCT/ISA/237)” of PCT/JP2020/008324, dated May 19, 2020, with English translation thereof, pp. 1-8.
“Office Action of Japan Counterpart Application” with English translation thereof, dated Oct. 5, 2021, p. 1-p. 6.

* cited by examiner

POLYMER AND METHOD FOR PRODUCING THE SAME, GAS SEPARATION MEMBRANE, GAS SEPARATION MODULE, AND GAS SEPARATION APPARATUS USING THE POLYMER, AND M-PHENYLENEDIAMINE COMPOUND

CROSS-REFERENCE TO RELATED APPLICATIONS

This application is a Continuation of PCT International Application No. PCT/JP2020/008324 filed on Feb. 28, 2020, which claims priorities under 35 U.S.C. § 119 (a) to Japanese Patent Application No. 2019-035097 filed in Japan on Feb. 28, 2019 and Japanese Patent Application No. 2019-135161 filed in Japan on Jul. 23, 2019. Each of the above applications is hereby expressly incorporated by reference, in its entirety, into the present application.

BACKGROUND OF THE INVENTION

1. Field of the Invention

The present invention relates to a polymer having a m-phenylenediamine skeleton and a method for producing the polymer, a gas separation membrane, a gas separation module, and a gas separation apparatus that use the polymer, and a m-phenylenediamine compound.

2. Description of the Related Art

Materials formed of polymer compounds each have gas permeability unique to the individual materials. On the basis of this property, selective permeation and separation of a desired gas component can be performed by using a membrane formed of a particular polymer compound. Regarding the industrial applications of such a gas separation membrane, in relation to the issues of global warming, separation and recovery of carbon dioxide from large-scale sources of carbon dioxide emission have been examined in thermal power plants, cement plants, blast furnaces in steel mills, and the like. In addition, natural gas and biogas (gas generated by fermentation or anaerobic digestion of, for example, excrement of organisms, organic fertilizers, biodegradable substances, sewage, garbage, and energy crops) are a mixed gas mainly containing methane and carbon dioxide, and use of a gas separation membrane has been examined as means for removing impurities such as carbon dioxide from the mixed gas.

For purification of natural gas with a gas separation membrane, high gas permeability and high gas separation selectivity are required to more efficiently separate an intended gas. To achieve this, various membrane materials have been examined. As part of this examination, a gas separation membrane that uses a polyimide compound has been examined. For example, JP2015-083296A discloses a polyimide compound having a diamine component obtained by introducing a particular polar group to a particular site of m-phenylenediamine. According to JP2015-083296A, by forming a gas separation layer of a gas separation membrane using the polyimide compound, both gas permeability and gas separation selectivity can be improved, and the deterioration of performance due to plasticizing components in the gas can also be suppressed.

To provide a practical gas separation membrane, sufficient gas permeability needs to be achieved by thinning the gas separation layer and also intended gas separation selectivity needs to be achieved. The method for thinning the gas separation layer is a method in which a polymer compound such as a polyimide compound is subjected to a phase separation process to obtain an asymmetric membrane, and a portion that contributes to separation is formed as a thin layer referred to as a dense layer or a skin layer. In this asymmetric membrane, a portion other than the dense layer is allowed to function as a support layer that provides mechanical strength of the membrane.

In addition to the asymmetric membrane, a form of a composite membrane is also known in which a gas separation layer having a gas separation function and a support layer contributing to mechanical strength are separately provided, and the gas separation layer having a gas separation function is formed as a thin layer on the gas-permeable support layer.

SUMMARY OF THE INVENTION

In general, the gas permeability and the gas separation selectivity are in a trade-off relationship. Therefore, either of the gas permeability or the gas separation selectivity of the gas separation layer can be improved by adjusting, for example, copolymerization components of a polyimide compound used for the gas separation layer. However, it is difficult to achieve both the characteristics at a high level. Furthermore, if the amount of a plasticizing component in a natural gas is small, the membrane is dried and densified as opposed to plasticization when used for a long time, which impairs the gas permeability. Therefore, the gas separation membrane is required to have characteristics in which the gas permeability can be sufficiently maintained even under severe dry conditions.

It is an object of the present invention to provide a gas separation membrane which has high gas permeability and high gas separation selectivity and whose gas permeability is not easily deteriorated even when exposed to severe dry conditions, and a gas separation module and a gas separation apparatus that have the gas separation membrane. It is also an object of the present invention to provide a functional polymer suitable for a gas separation layer of the gas separation membrane and a method for producing the polymer, and a diamine compound suitable as a raw material for the polymer.

The above objects of the present invention are achieved by the following means.

[1]

A polymer has a constituent component represented by formula (I) below.

Formula (I)

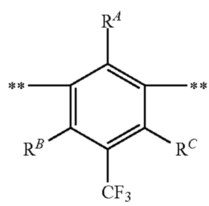

In the formula (I), $R^A$, $R^B$, and $R^C$ represent a hydrogen atom, an alkyl group having 1 to 4 carbon atoms, or a halogen atom, At least one of $R^A$, $R^B$, or $R^C$ represents an alkyl group having 1 to 4 carbon atoms or a halogen atom. The alkyl group having 1 to 4 carbon atoms is not trifluoromethyl, and ** represents linking sites.

[2]

In the polymer according to [1], the constituent component represented by the formula (I) is a component derived from a diamine.

[3]

In the polymer according to [1] or [2], the at least one of $R^A$, $R^B$, or $R^C$ represents an alkyl group having 1 to 4 carbon atoms.

[4]

In the polymer according to any one of [1] to [3], the polymer is a polyimide compound, a polyurethane compound, a polyurea compound, or a polyamide compound.

[5]

A method for producing the polymer according to any one of [1] to [4] includes obtaining a polymer using a m-phenylenediamine compound represented by formula (Ia) below as a raw material.

Formula (Ia)

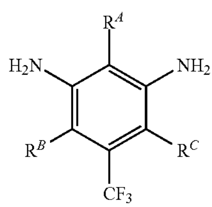

In the formula (Ia), $R^A$, $R^B$, and $R^C$ have the same meaning as $R^A$, $R^B$, and $R^C$ in the formula (I), respectively.

[6]

A gas separation membrane has a gas separation layer including the polymer according to any one of [1] to [4].

[7]

A gas separation membrane includes, as a polymer for a gas separation layer, a polyimide compound having a constitutional unit represented by formula (II) below.

Formula (II)

In the formula (II), $R^A$, $R^B$, and $R^C$ represent a hydrogen atom, an alkyl group having 1 to 4 carbon atoms, or a halogen atom. At least one of $R^A$, $R^B$, or $R^C$ represents an alkyl group having 1 to 4 carbon atoms or a halogen atom. The alkyl group having 1 to 4 carbon atoms is not trifluoromethyl.

R represents a group represented by any one of formulae (I-1) to (I-28) below. $X^1$ to $X^3$ represent a single bond or a divalent linking group, L represents —CH═CH— or —$CH_2$—, $R^1$ and $R^2$ represent a hydrogen atom or a substituent, and * represents bonding sites with carbonyl groups in the formula (II).

(I-1)

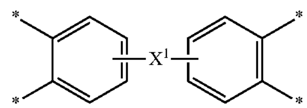

(I-2)

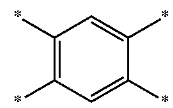

(I-3)

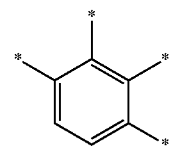

(I-4)

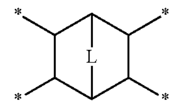

(I-5)

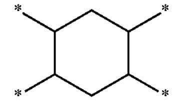

(I-6)

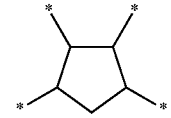

(I-7)

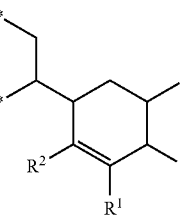

(I-8)

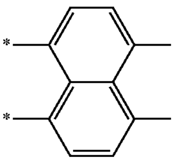

(I-9)

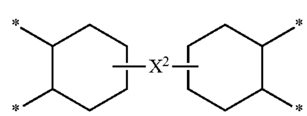

(I-10)

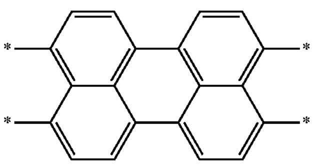

(I-11)

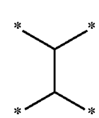

-continued

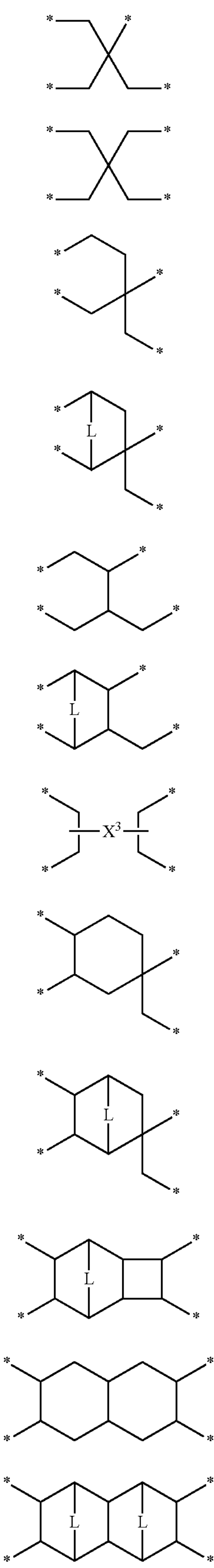

-continued

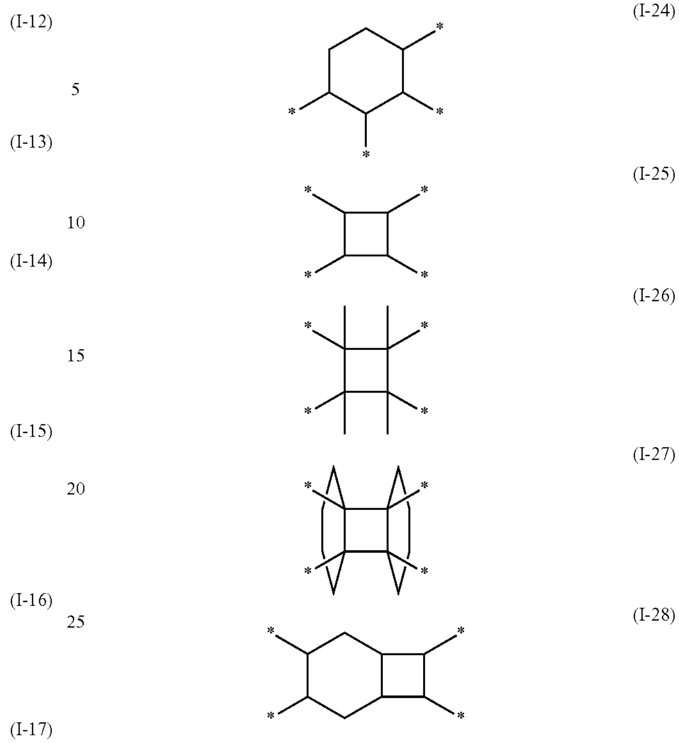

[8]

In the gas separation membrane according to [7], the at least one of $R^A$, $R^B$, or $R^C$ represents the alkyl group having 1 to 4 carbon atoms.

[9]

In the gas separation membrane according to any one of [6] to [8], the gas separation membrane is a gas separation composite membrane having the gas separation layer on an upper side of a gas permeable support layer.

[10]

The gas separation membrane according to any one of [6] to [9] is used for selective permeation of carbon dioxide in a gas including carbon dioxide and methane.

[11]

A gas separation module has the gas separation membrane according to any one of [6] to [10].

[12]

A gas separation apparatus has the gas separation membrane according to any one of [6] to [10].

A m-phenylenediamine compound is represented by formula (Ia-1) below.

Formula (Ia-1)

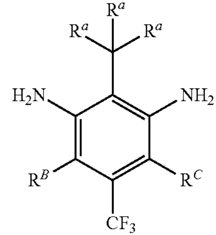

In the formula (Ia-1), $R^a$ represents a hydrogen atom, an alkyl group having 1 to 3 carbon atoms, a halogen atom, a hydroxy group, or an alkoxy group having 1 to 3 carbon atoms. —$C(R^a)_3$ has 1 to 4 carbon atoms and is not trifluoromethyl.

$R^B$ and $R^C$ represent a hydrogen atom, an alkyl group having 1 to 4 carbon atoms, or a halogen atom. The alkyl group that is represented by $R^B$ and $R^C$ and has 1 to 4 carbon atoms is not trifluoromethyl.

In this specification, every numerical range expressed using "to" means a range including numerical values before and after "to" as the lower and upper limits.

In this specification, when a plurality of substituents and linking groups (hereafter referred to as substituents and the like) are represented by particular symbols or when a plurality of substituents and the like are simultaneously or alternatively defined, the substituents and the like may be the same as or different from each other. The same also applies to the definition of the number of substituents and the like. When a polymer has a plurality of constituent components shown in the same manner, the constituent components may be the same as or different from each other.

In this specification, substituents (also linking groups) whose substitution or unsubstitution is not explicitly stated may have any substituent as long as desired effects are not impaired. The same applies to compounds whose substitution or unsubstitution is not explicitly stated.

The gas separation membrane, the gas separation module, and the gas separation apparatus according to embodiments of the present invention have high gas permeability and high gas separation selectivity, and have gas permeability sufficiently maintained even when a gas separation layer is exposed to severe dry conditions. The polymer according to an embodiment of the present invention can be used as a material for the gas separation layer and various functional polymers because the constituent components of the polymer have distinctive strictures.

DESCRIPTION OF THE PREFERRED EMBODIMENTS

Figure 1:
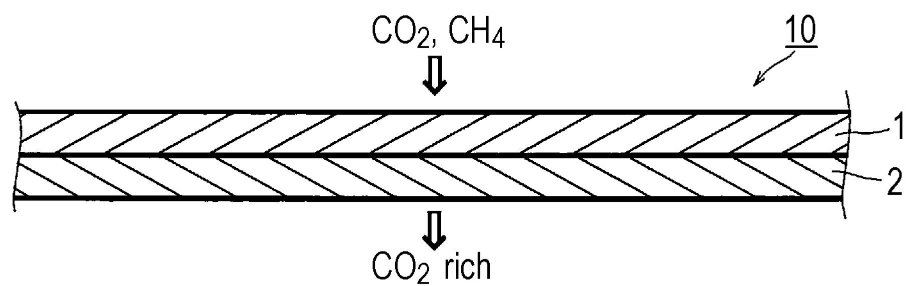
FIG. 1 is a sectional view schematically illustrating a gas separation composite membrane according to one embodiment of the present invention.

Preferred embodiments of the present invention will be described

Polymer

The polymer (polymer compound) according to an embodiment of the present invention has a constituent component represented by formula (I) below.

Formula (I)

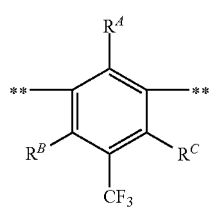

In the formula (I), $R^A$, $R^B$, and $R^C$ represent a hydrogen atom, an alkyl group having 1 to 4 carbon atoms (preferably an alkyl group having 1 to 3 carbon atoms), or a halogen atom. ** represents linking sites through which the constituent component is incorporated into the polymer.

In the formula (I), at least one of $R^A$, $R^B$, or $R^C$ represents an alkyl group having 1 to 4 carbon atoms or a halogen atom. In particular, at least $R^A$ preferably represents an alkyl group having 1 to 4 carbon atoms or a halogen atom.

Examples of the halogen atom that may be represented by $R^A$, $R^B$, and $R^C$ include a fluorine atom, a chlorine atom, a bromine atom, and an iodine atom. The halogen atom is pmferably a chlorine atom or a bromine atom and more preferably a chlorine atom.

In the constituent component represented by the formula (I), preferably, at least one of $R^A$, $R^B$, or $R^C$ represents an alkyl group having 1 to 4 carbon atoms. More preferably, at least $R^A$ represents an alkyl group having 1 to 4 carbon atoms.

The alkyl group that has 1 to 4 carbon atoms and may be represented by $R^A$, $R^B$, and $R^C$ may have a substituent. That is, the alkyl group that has 1 to 4 carbon atoms and may be represented by $R^A$, $R^B$, and $R^C$ may be a substituted alkyl group having 1 to 4 carbon atoms (the number of carbon atoms in the substituted alkyl group is a sum of the number of carbon atoms in the alkyl group and the number of carbon atoms in the substituent). However, the alkyl group that has 1 to 4 carbon atoms and may be represented by $R^A$, $R^B$, and $R^C$ is preferably not trifluoromethyl.

When the alkyl group having 1 to 4 carbon atoms is trifluoromethyl, the monomer that results in such a constituent component tends to be not easily polymerized because of both steric influence and electrical influence. For example, when the constituent component represented by the formula (I) is a diamine component and $R^A$, $R^B$, or $R^C$ represents trifluoromethyl, the diamine monomer that results in this diamine component has poor polymerization efficiency.

The alkyl group that has 1 to 4 carbon atoms and may be represented by $R^A$, $R^B$, and $R^C$ is also preferably a substituted alkyl group having one or two substituents. That is, the alkyl group that has 1 to 4 carbon atoms and may be represented by $R^A$, $R^B$, and $R^C$ is also preferably an unsubstituted alkyl group, a monosubstituted alkyl group obtained by substituting one hydrogen atom constituting an unsubstituted alkyl group with a substituent, or a disubstituted alkyl group obtained by substituting two hydrogen atoms constituting an unsubstituted alkyl group with substituents.

When the alkyl group having 1 to 4 carbon atoms is a substituted alkyl group, the substituent in this substituted alkyl group is, for example, a halogen atom, a hydroxy group, an alkoxy group (preferably having 1 to 3 carbon atoms), or an acyloxy group (preferably having 1 to 3 carbon atoms) and is preferably a halogen atom.

The alkyl group that has 1 to 4 carbon atoms and may be represented by $R^A$, $R^B$, and $R^C$ is preferably an unsubstituted alkyl group.

The alkyl group that has 1 to 4 carbon atoms and may be represented by $R^A$, $R^B$, and $R^C$ is preferably ethyl or methyl, more preferably unsubstituted ethyl or unsubstituted methyl, and further preferably unsubstituted methyl.

The polymer according to an embodiment of the present invention exhibits desired characteristics or functions due to the unique structure represented by the formula (I). For example, the polymer is allowed to have low dielectric constant and higher transparency. The reason for this is unclear, but is probably as follows. The trifluoromethyl group positioned at a particular site of the constituent component represented by the formula (I) contributes to reduction in dielectric constant and improvement in transparency of the polymer. Furthermore, when at least one of $R^A$, $R^B$, or $R^C$ in the formula (1) represents a particular short-chain alkyl group or a halogen atom, the planarity or packing property of the polymer is suppressed to some degree to appropriately form cavities in the polymer, which effectively contributes to reduction in dielectric constant and improvement in transparency.

On the basis of the above characteristics, the polymer having the constituent component represented by the formula (I) can be used as various functional polymers. For example, the polymer according to an embodiment of the present invention can be suitably used as a polymer for, for example, transparent heat-resistant resins, low dielectric constant resins, materials for high frequency, and moisture-proof coating materials.

The polymer according to an embodiment of the present invention is also suitably used as a material for gas separation layers of gas separation membranes. By using the polymer according to an embodiment of the present invention, even when a thin gas separation layer is formed, a desired gas component in a mixed gas is allowed to permeate the gas separation membrane with high selectivity, which can achieve both high gas permeability and high gas separation selectivity. This gas separation membrane includes a gas separation layer whose gas permeability can be sufficiently maintained even under severe dry conditions. This is probably as follows. The trifluoromethyl group suppresses the cohesion of the polymer, and $R^A$, $R^B$, and $R^C$ also suppress the planarity or the packing property, thereby forming sufficient cavities in the polymer to the degree that the gas separation selectivity is not impaired. This imparts a large free volume, and the free volume can be sufficiently maintained even under severe dry conditions. Therefore, the gas separation membrane that uses the polymer according to an embodiment of the present invention for the gas separation layer is particularly suitably used in, for example, a natural gas field with a small amount of plasticizing component.

When the polymer according to an embodiment of the present invention is used as a material for the gas separation layer, the polymer is preferably a polyimide compound as described later.

The constituent component represented by the formula (I) is preferably a constituent component derived from a m-phenylenediamine compound represented by formula (Ia) below. That is, the polymer according to an embodiment of the present invention is preferably obtained using, as a synthetic raw material, the m-phenylenediamine compound represented by the formula (Ia) below.

Formula (Ia)

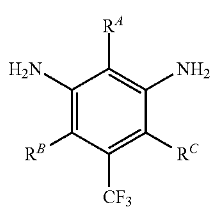

In the formula (Ia), $R^A$, $R^B$, and $R^C$ respectively have the same meaning as $R^A$, $R^B$, and $R^C$ in the formula (I), and the preferred forms are also the same.

The polymer according to an embodiment of the present invention can be obtained as a polyimide compound by subjecting the m-phenylenediamine compound represented by the formula (Ia) and tetracarboxylic dianhydride to polycondensation. The polyimide compound can be synthesized by a typical method, except for raw materials used. The synthesis can be performed by appropriately employing a method described in general books (e.g., Yoshio Imai, Rikio Yokota, "Latest Polyimides—Fundamentals and Applications—", NTS Inc., Aug. 25, 2010, pp. 3 to 49).

Furthermore, the amino group of the m-phenylenediamine compound represented by the general formula (Ia) can be isocyanated and then reacted with a diol compound to obtain a polyurethane compound. The polyurethane compound can be synthesized by a typical method, except for raw materials used. For example, the synthesis can be performed with reference to "Polymer Experiments 5, Polycondensation and Polyaddition", edited by editorial committee members of polymer experiments in The Society of Polymer Science, Kyoritsu Shuppan Co., Ltd., 1980.

A polyurea compound can be obtained by isocyanating the m-phenylenediamine compound represented by the general formula (Ia) and then causing a reaction with a diamine compound or by causing a reaction of the m-phenylenediamine compound represented by the general formula (Ia) and a diisocyanate compound. The polyurea compound can be synthesized by a typical method, except for raw materials used. For example, the synthesis can be performed with reference to "Polymer Experiments 5, Polycondensation and Polyaddition", edited by editorial committee members of polymer experiments in The Society of Polymer Science, Kyoritsu Shuppan Co., Ltd., 1980.

A polyamide compound can be Obtained by subjecting the m-phenylenediamine compound represented by the general formula (Ia) and a dicarboxylic acid compound to polycondensation. The polyamide compound can be synthesized by a typical method, except for raw materials used. For example, the synthesis of the polyamide compound can be performed with reference to "Polymer Experiments 5, Polycondensation and Polyaddition", edited by editorial committee members of polymer experiments in The Society of Polymer Science, Kyoritsu Shuppan Co., Ltd., 1980.

In the present invention, the molecular weight of the "polymer" is not particularly limited as long as the above structure is satisfied. For example, the molecular weight can be set to 1000 to 1000000, preferably 10000 to 500000, more preferably 20000 to 300000. Herein, when the molecular weight is 1000 or more, the molecular weight is a weight-average molecular weight.

Gas Separation Membrane

The gas separation membrane according to an embodiment of the present invention has a gas separation layer containing the above-described polymer according to an embodiment of the present invention. The polymer according to an embodiment of the present invention is believed to have a large free volume that can be maintained even under severe dry conditions as described above. By using this polymer as a material for the gas separation layer, both high gas permeability and high gas separation selectivity can be achieved and gas separation performance can be sufficiently maintained even in a severe environment.

The gas separation layer of the gas separation membrane according to an embodiment of the present invention is preferably formed of a polyimide compound having at least the constituent component represented by the formula (I). The polyimide compound preferably has at least a constitutional unit represented by formula (II) below.

Formula (II)

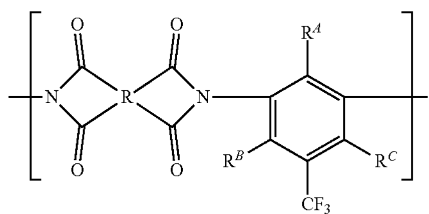

In the formula (II), $R^A$, $R^B$, and $R^C$ respectively have the same meaning as $R^A$, $R^B$, and $R^C$ in the formula (I), and the preferred forms are also the same.

In the formula (II), R represents a group having a structure represented by any one of formulae (I-1) to (I-28). Herein, $X^1$ to $X^3$ represent a single bond or a divalent linking group, L represents —CH═CH— or —$CH_2$—, $R^1$ and $R^2$ represent a hydrogen atom or a substituent, and * represents bonding sites with carbonyl groups in the formula (II). R preferably represents a group represented by the formula (I-1), (I-2), or (I-4), more preferably a group represented by the formula (I-1) or (I-4), and particularly preferably a group represented by the formula (I-1).

(I-1)

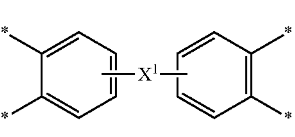

(I-2)

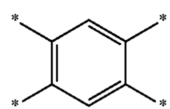

(I-3)

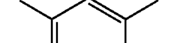

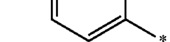

(I-4)

(I-5)

(I-6)

(I-7)

-continued (I-8)

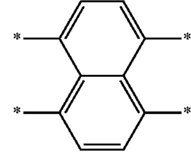

(I-9)

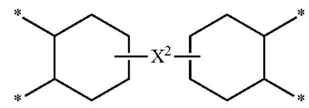

(I-10)

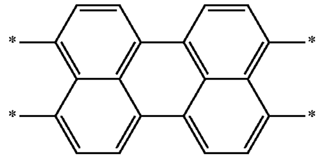

(I-11)

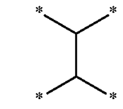

(I-12)

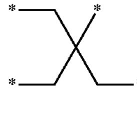

(I-13)

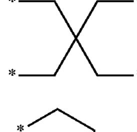

(I-14)

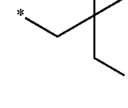

(I-15)

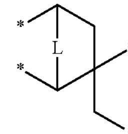

(I-16)

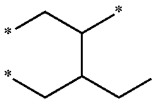

(I-17)

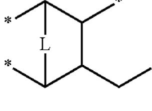

(I-18)

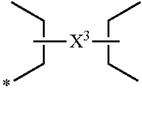

(I-19)

-continued

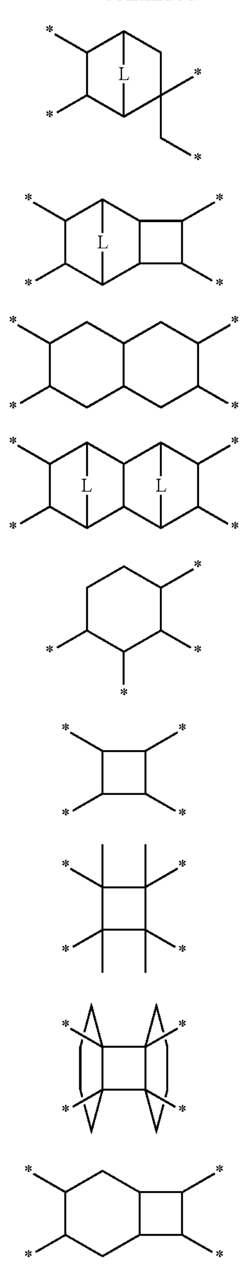

In the formulae (I-1), (I-9), and (I-18), $X^1$ to $X^3$ represent a single bond or a divalent linking group. The divalent linking group is preferably —$C(R^X)_2$— (each $R^X$ represents a hydrogen atom or a substituent, where $R^X$ representing substituents may be linked to each other to form a ring), —O—, —$SO_2$—, —C(═O)—, —S—, —$NR^Y$— ($R^Y$ represents a hydrogen atom, an alkyl group (preferably a methyl group or an ethyl group), or an aryl group (preferably a phenyl group)), —$C_6H_4$— (phenylene group), or a combination of the foregoing and more preferably a single bond or —$C(R^X)_2$—. When each $R^X$ represents a substituent, the substituent is specifically a group selected from the substituent group Z described later. The substituent is preferably an alkyl group (the preferred range is the same as that of alkyl groups shown in the substituent group Z described later), more preferably an alkyl group having a halogen atom as a substituent, and particularly preferably trifluoromethyl. In the formula (I-18), $X^3$ links to one of two carbon atoms illustrated on the left side and one of two carbon atoms illustrated on the right side.

In the formulae (I-4), (I-15), (I-17), (I-20), (I-21), and (I-23), L represents —CH═CH— or —$CH_2$—.

In the formula (I-7), $R^1$ and $R^2$ represent a hydrogen atom or a substituent. The substituent is a group selected from the substituent group Z described later. $R^1$ and $R^2$ may bond to each other to form a ring.

$R^1$ and $R^2$ preferably represent a hydrogen atom or an alkyl group, more preferably a hydrogen atom, a methyl group, or an ethyl group, and further preferably a hydrogen atom.

The carbon atoms in the formulae (I-1) to (I-28) may further have a substituent as long as the effects of the present invention are not impaired. In the present invention, the form of carbon atoms having a substituent is also included in the group represented by any of the formulae (I-1) to (I-28). This substituent is specifically a group selected from the substituent group Z described later, and is preferably an alkyl group or an aryl group.

In the polyimide compound used in the present invention, the content of the structural unit represented by the formula (II) is preferably 20 mass % or more, more preferably 30 mass % or more, and further preferably 40 mass % or more. The polyimide compound used in the present invention is also preferably constituted by the structural unit represented by the formula (II).

The polyimide compound may have a constitutional unit represented by formula (III) or (IV) below in addition to the constitutional unit represented by the formula (II). Herein, the constitutional unit represented by the formula (III) below does not include the constitutional unit represented by the formula (II). The polyimide compound may include one or two or more constitutional units represented by formula (III) or (IV).

Formula (III)

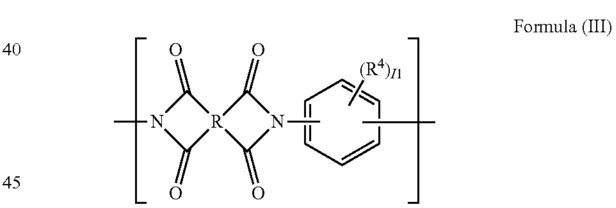

Formula (IV)

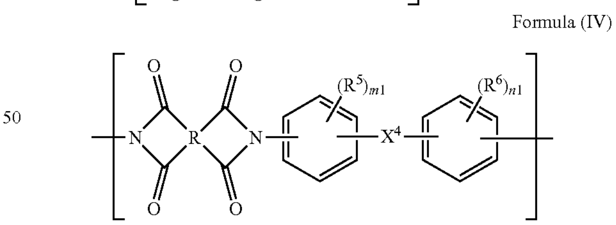

In the formula (III) and (IV), R has the same meaning as R in the formula (II), and the preferred form is also the same. $R^4$ to $R^6$ represent a substituent. The substituent is a group selected from the substituent group Z described later.

$R^4$ preferably represents an alkyl group, a carboxy group, a sulfamoyl group, a carbamoyl group, or a halogen atom. The number of $R^4$ is indicated by l1, which is an integer of 0 to 4. When $R^4$ represents an alkyl group, the number of carbon atoms of the alkyl group is preferably 1 to 10, more preferably 1 to 5, and further preferably 1 to 3, and the alkyl group is more preferably methyl, ethyl, or trifluoromethyl. The constitutional unit represented by the formula (III)

preferably has a carboxy group or a sulfamoyl group. When the constitutional unit represented by the formula (III) has a carboxy group or a sulfamoyl group, the number of carboxy groups or sulfamoyl groups in the formula (III) is preferably one.

In the formula (III), two linking sites of the diamine component (i.e., a phenylene group that may have $R^4$) that are used for incorporation into the polyimide compound are preferably located at meta positions or para positions and more preferably located at meta positions.

$R^5$ and $R^6$ preferably represent an alkyl group or a halogen atom or preferably represent groups that are linked to each other to form a ring together with $X^4$. Alternatively, two $R^5$ are preferably linked to form a ring or two $R^6$ are preferably linked to form a ring. The structure in which $R^5$ and $R^6$ are linked is not particularly limited and is preferably a single bond, —O—, or —S—. Each of m1 and n1 representing the number of $R^5$ and the number of $R^6$ is an integer of 0 to 4, preferably 0 to 3, more preferably 0 to 2, and further preferably 0 or 1. When $R^5$ and $R^6$ represent an alkyl group, the number of carbon atoms in the alkyl group is preferably 1 to 10, more preferably 1 to 5, and further preferably 1 to 3, and the alkyl group is more preferably methyl, ethyl, or trifluoromethyl.

In the formula (IV), two linking sites of two phenylene groups (i.e,, two phenylene groups that may have $R^5$ and $R^6$) in the diamine component that are used for incorporation into the polyimide compound are located at meta positions or para positions with respect to the linking sites of $X^4$.

$X^4$ has the same meaning as $X^1$ in the formula (I-1), and the preferred form is also the same.

In the structure of the polyimide compound used in the present invention, the proportion of the molar quantity of the constitutional unit represented by the formula (II) is preferably 40 to 100 mol %, more preferably 50 to 100 mol %, more preferably 70 to 100 mol %, more preferably 80 to 100 mol %, and more preferably 90 to 100 mol % relative to the total molar quantity of the constitutional unit represented by the formula (II), the constitutional unit represented by the formula (III), and the constitutional unit represented by the formula (IV). When the proportion of the molar quantity of the constitutional unit represented by the formula (II) is 100 mol % relative to the total molar quantity of the constitutional unit represented by the formula (II), the constitutional unit represented by the formula (III), and the constitutional unit represented by the formula (IV), the polyimide compound does not have the constitutional unit represented by the formula (III) or the constitutional unit represented by the formula (IV).

The polyimide compound used in the present invention is constituted by the constitutional unit represented by the formula (II). Alternatively, when constitutional units other than the constitutional unit represented by the formula (II) are contained, the balance except for the constitutional unit represented by the formula (II) is preferably constituted by the constitutional unit represented by the formula (III) or the formula (IV). Herein, the phrase "constituted by the constitutional unit represented by the formula (III) or the formula (IV)" means that the following three forms are included: the form constituted by the constitutional unit represented by the formula (III), the form constituted by the constitutional unit represented by the formula (IV), and the form constituted by the constitutional unit represented by the formula (III) and the constitutional unit represented by the formula (IV).

Substituent Group Z:

Examples of the substituent group z include alkyl groups (alkyl groups preferably having 1 to 30 carbon atoms, more preferably having 1 to 20 carbon atoms, and particularly preferably having 1 to 10 carbon atoms, such as methyl, ethyl, iso-propyl, tert-butyl, n-octyl, n-decyl, and n-hexadecyl), cycloalkyl groups (cycloalkyl groups preferably having 3 to 30 carbon atoms, more preferably having 3 to 20 carbon atoms, and particularly preferably having 3 to 10 carbon atoms, such as cyclopropyl, cyciopentyl, and cyclohexyl), alkenyl groups (alkenyl groups preferably having 2 to 30 carbon atoms, more preferably having 2 to 20 carbon atoms, and particularly preferably having 2 to 10 carbon atoms, such as vinyl, allyl, 2-butenyl, and 3-pentenyl), alkynyl groups (alkynyl groups preferably having 2 to 30 carbon atoms, more preferably having 2 to 20 carbon atoms, and particularly preferably 2 to 10 carbon atoms, such as propargyl and 3-pentynyl), aryl groups (aryl groups preferably having 6 to 30 carbon atoms, more preferably having 6 to 20 carbon atoms, and particularly preferably having 6 to 12 carbon atoms, such as phenyl, p-methylphenyl, naphthyl, and anthranil), amino groups (including amino groups, alkylamino groups, arylamino groups, and heterocyclic amino groups, amino groups preferably having 0 to 30 carbon atoms, more preferably having 0 to 20 carbon atoms, and particularly preferably having 0 to 10 carbon atoms, such as amino, methylamino, dimethyl amino, diethylamine, dibenzylamino, diphenylamino, and ditolylamino), alkoxv groups (alkoxy groups preferably having 1 to 30 carbon atoms, more preferably having 1 to 20 carbon atoms, and particularly preferably having 1 to 10 carbon atoms, such as methoxy, ethoxy, butoxy, and 2-ethylhexyloxy), aryloxy groups (aryloxy groups preferably having 6 to 30 carbon atoms, more preferably having 6 to 20 carbon atoms, and particularly preferably having 6 to 12 carbon atoms, such as phenyloxy, 1-naphthyloxy, and 2-naphthyloxy), heterocyclic oxy groups (heterocyclic oxy groups preferably having 1 to 30 carbon atoms, more preferably having 1 to 20 carbon atoms, and particularly preferably having 1 to 12 carbon atoms, such as pyridyloxy, pyrazyloxy, pyrimidyloxy, and quinolyloxy);

acyl groups (acyl groups preferably having 1 to 30 carbon atoms, more preferably having 1 to 20 carbon atoms, and particularly preferably having 1 to 12 carbon atoms, such as acetyl, benzoyl, formyl, and pivaloyl), alkoxycarbonyl groups (alkoxycarbonyl groups preferably having 2 to 30 carbon atoms, more preferably having 2 to 20 carbon atoms, and particularly preferably having 2 to 12 carbon atoms, such as methoxycarbonyl and ethoxycarbonyl), aryloxycarbonyl groups (aryloxycarbonyl groups preferably having 7 to 30 carbon atoms, more preferably having 7 to 20 carbon atoms, and particularly preferably having 7 to 12 carbon atoms, such as phenyloxycarbonyl), acyloxy groups (acyloxy groups preferably having 2 to 30 carbon atoms, more preferably having 2 to 20 carbon atoms, and particularly preferably having 2 to 10 carbon atoms, such as acetoxv and benzoyloxy), and acylamino groups (acylamino groups having 2 to 30 carbon atoms, more preferably having 2 to 20 carbon atoms, and particularly preferably having 2 to 10 carbon atoms, such as acetylamine and. benzoyl amino);

alkoxycarbonylamino groups (alkoxycarbonylamino groups preferably having 2 to 30 carbon atoms, more preferably having 2 to 20 carbon atoms, and particularly preferably having 2 to 12 carbon atoms, such as methoxycarbonylamino), aryloxycarbonylamino groups (aryloxycarbonylamino groups preferably having 7 to 30 carbon atoms, more preferably having 7 to 20 carbon atoms, and particularly preferably having 7 to 12 carbon atoms, such as phenyloxycarbonylamino), sulfonylamino groups (sulfonylamino groups preferably having 1 to 30 carbon atoms, more preferably having 1 to 20 carbon atoms, and particularly preferably· having 1 to 12 carbon atoms, such as methanesulfonylamino and benzenesulfonylamino), and sulfamoyl groups (sulfamoyl groups preferably having 0 to 30 carbon atoms, more preferably having 0 to 20 carbon atoms, and particularly preferably having 0 to 12 carbon atoms, such as sulfamoyl, methylsulfamoyl, dimethylsulfamoyl, and phenylsulfamoyl);

alkylthio groups (alkylthio groups preferably having 1 to 30 carbon atoms, more preferably having 1 to 20 carbon atoms, and particularly preferably having 1 to 12 carbon atoms, such as methylthio and ethylthio), arylthio groups (arylthio groups preferably having 6 to 30 carbon atoms, more preferably having 6 to 20 carbon atoms, and particularly preferably having 6 to 12 carbon atoms, such as phenylthio), heterocyclic thio groups (heterocyclic thio groups preferably having 1 to 30 carbon atoms, more preferably having 1 to 20 carbon atoms, and particularly preferably having 1 to 12 carbon atoms, such as pyridylthio, 2-benzimizolylthio, 2-benzoxazolylthio, and 2-benzothiazolyithio);

sulfonyl groups (sulfonyl groups preferably having 1 to 30 carbon atoms, more preferably having 1 to 20 carbon atoms, and particularly preferably having 1 to 12 carbon atoms, such as mesyl and tosyl), sulfinyl groups (sulfinyl groups preferably having 1 to 30 carbon atoms, more preferably having 1 to 20 carbon atoms, and particularly preferably having 1 to 12 carbon atoms, such as methanesulfinyl and benzenesulfinyl), ureido groups (ureido groups preferably having 1 to 30 carbon atoms, more preferably having 1 to 20 carbon atoms, and particulady preferably having 1 to 12 carbon atoms, such as ureido, methylureido, and phenylureido), phosphoramide groups (phosphoramide groups preferably having 1 to 30 carbon atoms, more preferably having 1 to 20 carbon atoms, and particularly preferably having 1 to 12 carbon atoms, such as diethylphosphoramide and phenylphosphoramide), a hydroxy group, a mercapto group, and a halogen atom (e.g., a fluorine atom, a chlorine atom, a bromine atom, and an iodine atom, more preferably a fluorine atom); and a cyano group, a carboxy group, an oxo group, a nitro group, a hydroxamic acid group, a sulfino group, a hydrazino group, an imino group, heterocyclic groups (3- to 7-membered ring heterocyclic groups are preferable, the heterocycle may be aromatic or non-aromatic, examples of the heteroatom contained in the heterocycle include a nitrogen atom, an oxygen atom, and a sulfur atom, the number of carbon atoms in each heterocyclic group is preferably 0 to 30 and more preferably 1 to 12, e.g., imidazolyl, pyridyl, quinolyl, furyl, thienyl, piperidyl, morpholino, benzoxazolyl, benzimidazolyl, benzothiazolyl, carbazolyl, and azepinyl), silyl groups (silyl groups preferably having 3 to 40 carbon atoms, more preferably having 3 to 30 carbon atoms, and particularly preferably having 3 to 24 carbon atoms, such as trimethylsilyl and triphenylsilyl), and silyloxy groups (silyloxy groups preferably having 3 to 40 carbon atoms, more preferably having 3 to 30 carbon atoms, and particularly preferably having 3 to 24 carbon atoms, such as trimethylsilyloxy and triphenylsilyloxy). These substituents may be further substituted with any one or more substituents selected from the substituent group Z described above.

In the present invention, when one structural site has a plurality of substituents, these substituents may be linked to each other to form a ring or may be fused with a part or the whole of the structural site to form an aromatic ring or an unsaturated heterocyclic ring.

When the compound, the substituent, or the like includes an alkyl group, an alkenyl group, and the like, they may be linear groups or branched groups or may be substituted or not substituted. When the compound, the substituent, or the like includes an aryl group, a heterocyclic group, and the like, they may be monocyclic or undergo annelation or may be substituted or not substituted.

In this specification, those simply referred to as substituents are selected from the substituent group Z unless otherwise specified. When only the name of each group is stated (e.g., "alkyl group" is simply stated), the preferred range and specific examples of the group corresponding to the substituent group Z are applied.

The molecular weight of the polyimide compound is preferably 10,000 to 1,000,000, more preferably 15,000 to 500,000, and further preferably 20,000 to 200,000 in terms of weight-average molecular weight.

in this specification, the molecular weight and the dispersity are measured by GPC (gel permeation chromatography) unless otherwise specified, and the molecular weight is a weight-average molecular weight in terms of polystyrene. The gel filling columns used in GPC is preferably a gel including an aromatic compound as a repeating unit and is, for example, a gel formed of a styrene-divinylbenzene copolymer. Two to six columns are preferably connected and used. Examples of a solvent used include ether solvents such as tetrahydrofuran and amide solvents such as N-methylpyrrolidinone. In the measurement, the flow velocity of the solvent is preferably in the range of 0.1 to 2 mL/min and most preferably in the range of 0.5 to 1.5 mL/min. When the measurement is performed within the above range, the measurement can be further efficiently performed without applying load to the instrument. The measurement temperature is preferably 10° C. to 50° C. and most preferably 20° C. to 40° C. The columns and carriers used can be appropriately selected in accordance with the physical properties of a polymer to be measured.

The polyimide compound can be synthesized by a typical method through condensation polymerization of a bifunctional acid anhydride having a particular structure (tetracarboxylic dianhydride) and a diamine having a particular structure as described above.

In the synthesis of the polyimide compound, the tetracarboxylic dianhydride, which is one of the raw materials, is preferably represented by formula (V) below.

Formula (V)

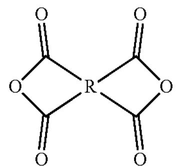

In the formula (V), R has the same meaning as R in the formula (II), and the preferred form is also the same.

The tetracarboxylic dianhydride used in the present invention is specifically exemplified below. In the structural formulae below, Ph represents phenyl.

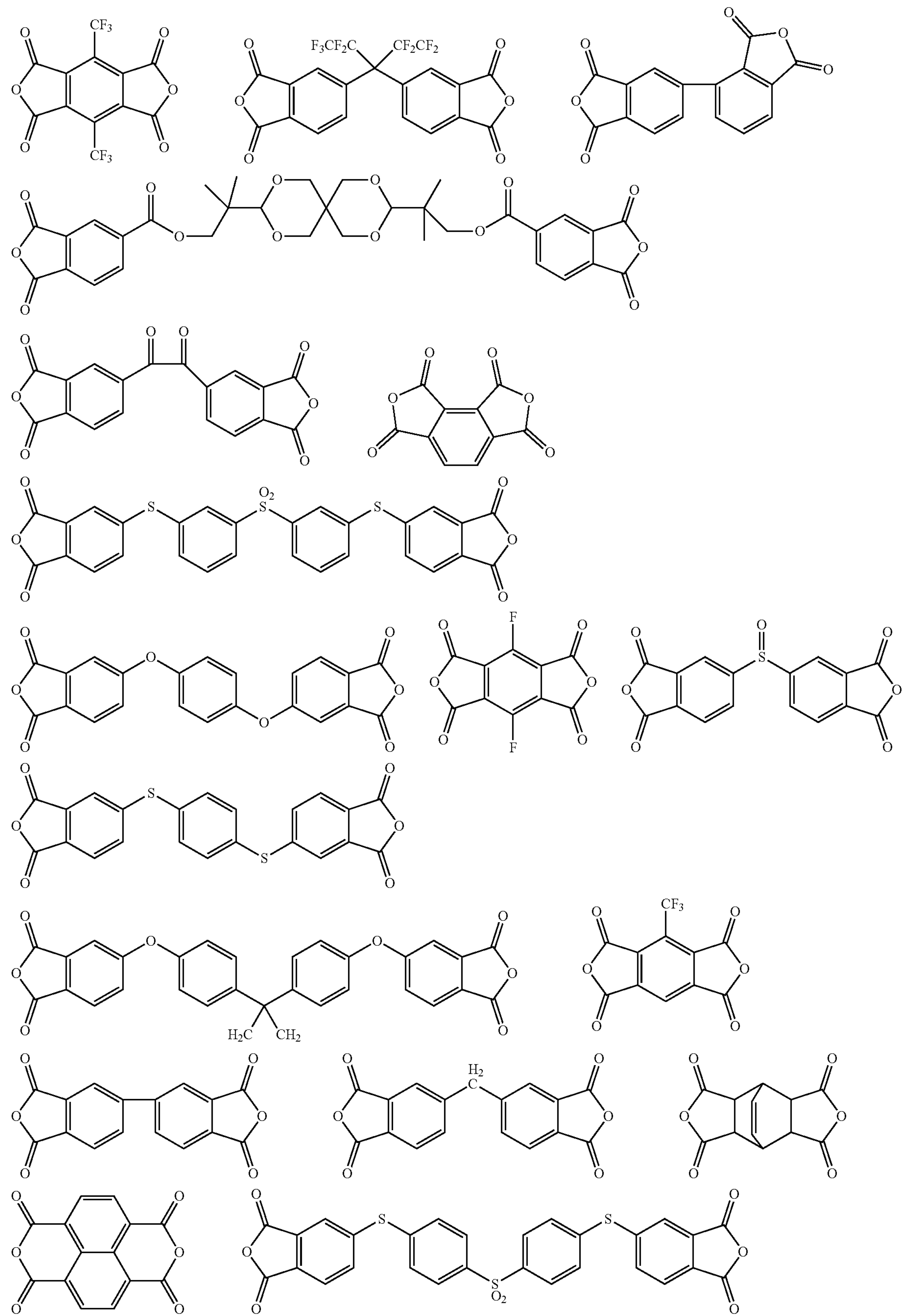
CF3
F3CF2C
CF2CF2
O2
F
H2C
CH2
H2
C

-continued
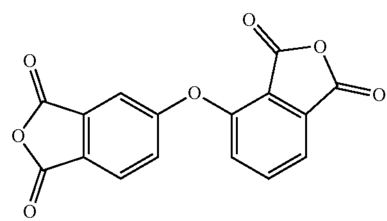
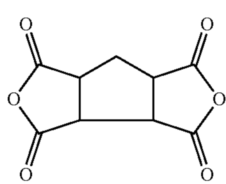
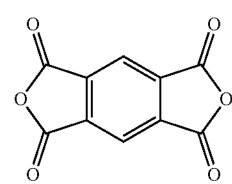
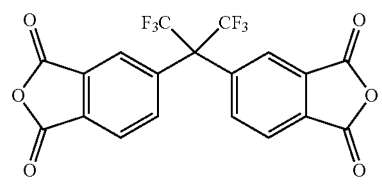
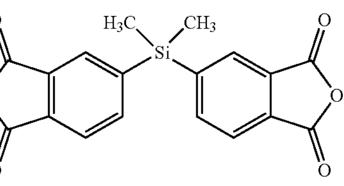
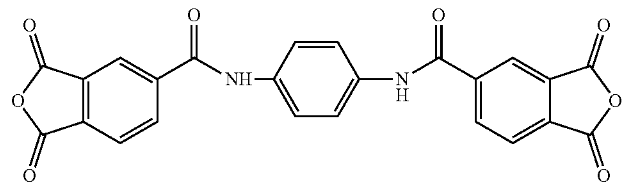
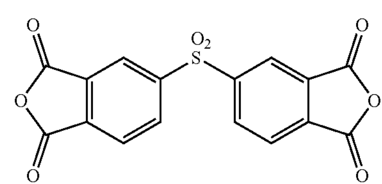
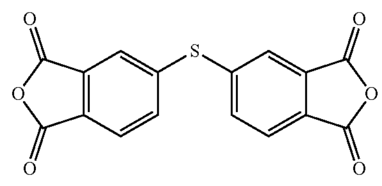
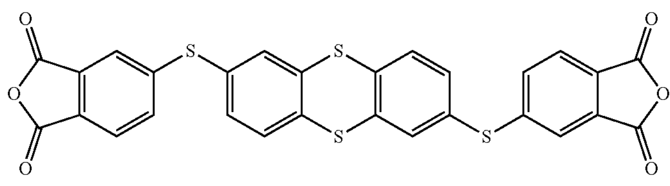
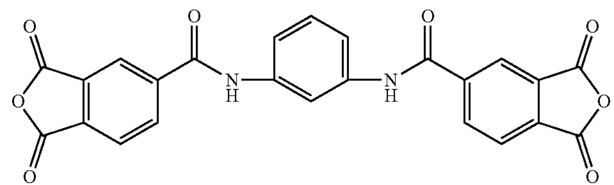
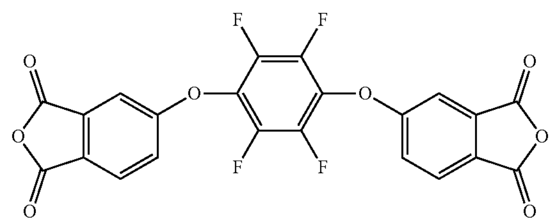
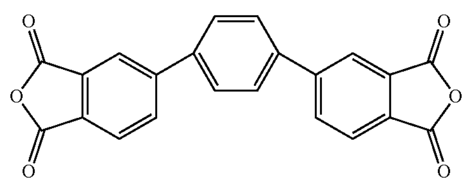
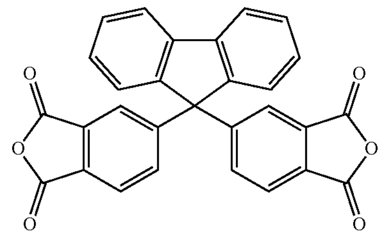
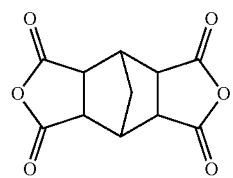
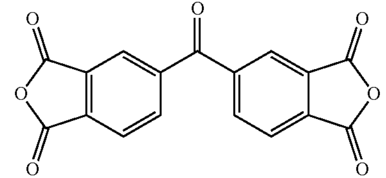
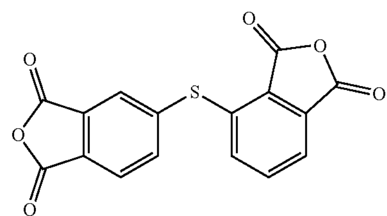
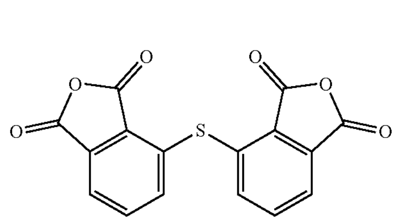
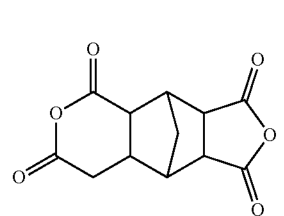

-continued
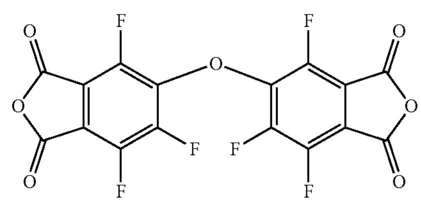
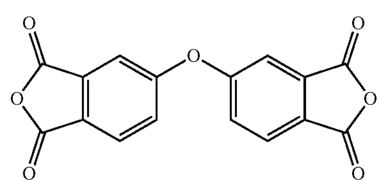
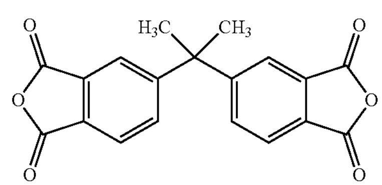
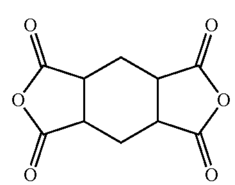
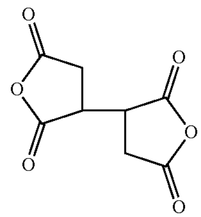
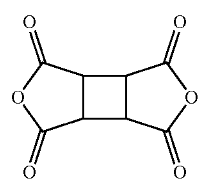
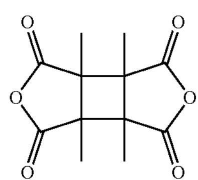
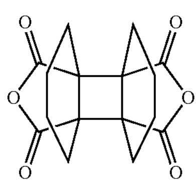
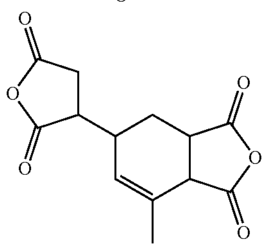
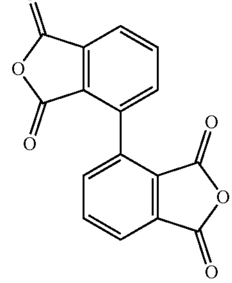
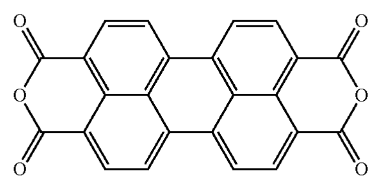
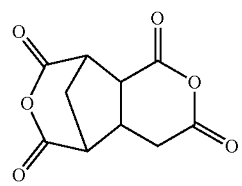
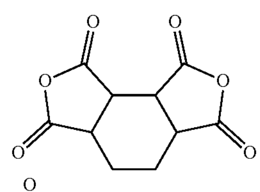
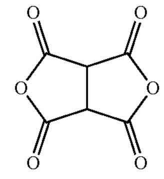
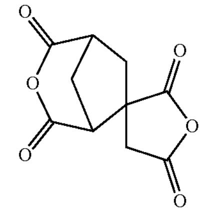
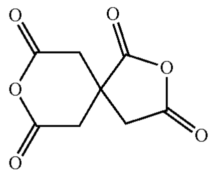
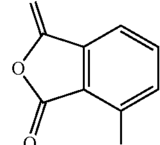
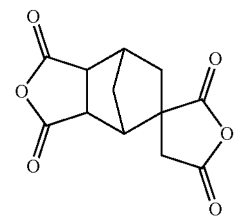
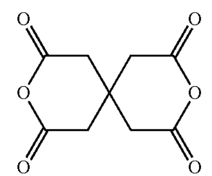
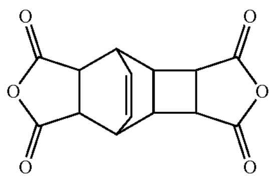
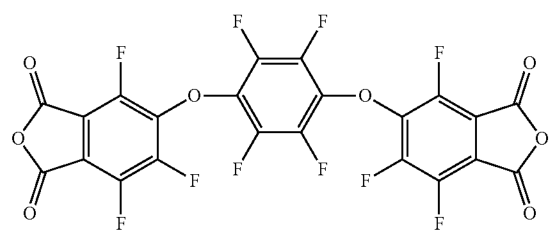
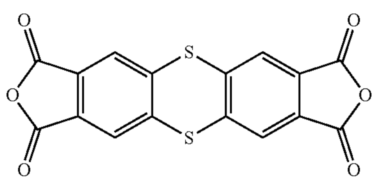

-continued
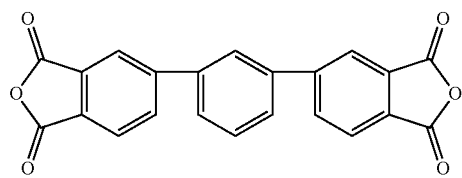
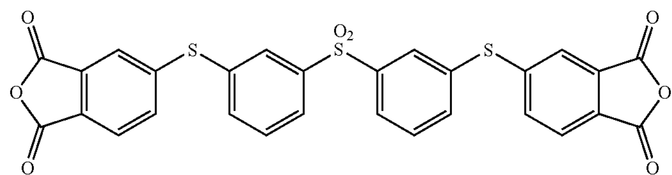
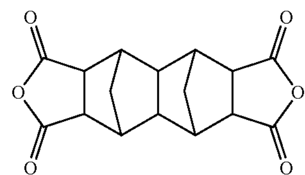
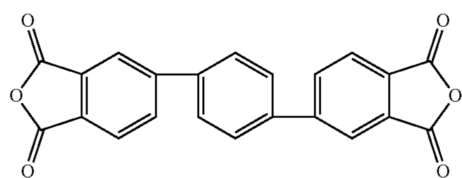
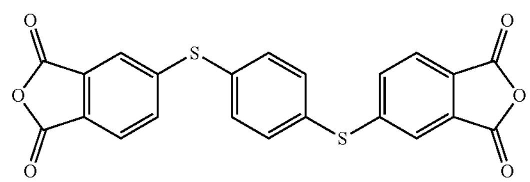
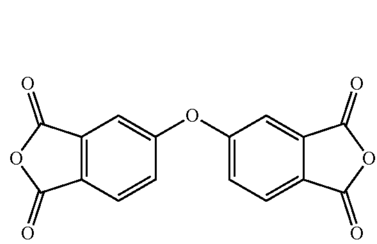
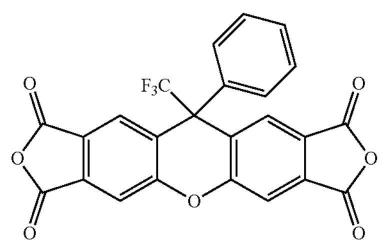
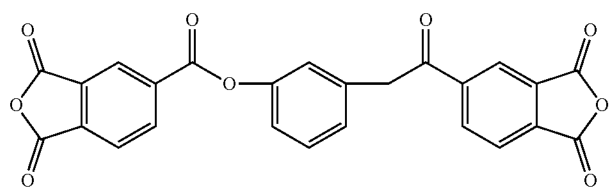
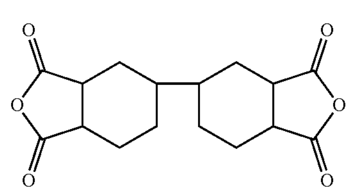
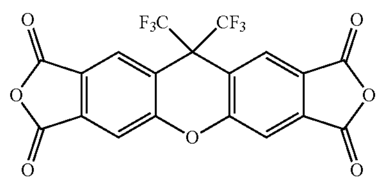
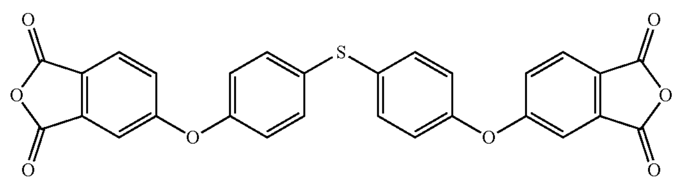
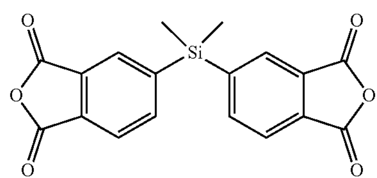
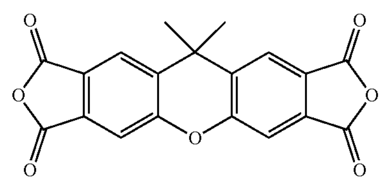
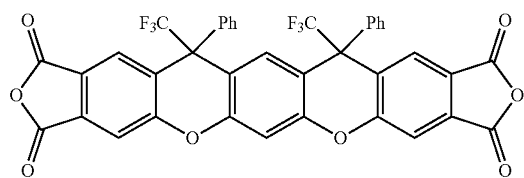
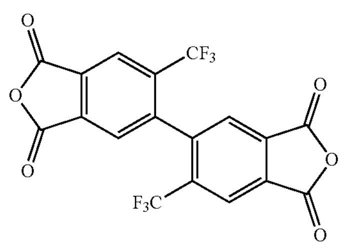

-continued

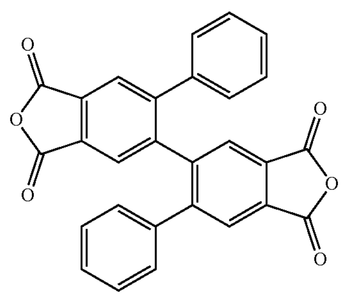

In the synthesis of the polyimide compound used in the present invention, at least one diamine compound, which is the other of the raw materials, is represented by the above formula (Ia).

Preferred specific examples of the diamine compound represented by the formula (Ia) are shown below, but the present invention is not limited thereto. In the structural formulae below, Me represents methyl, Et represents ethyl, and Pr represents n-propyl.

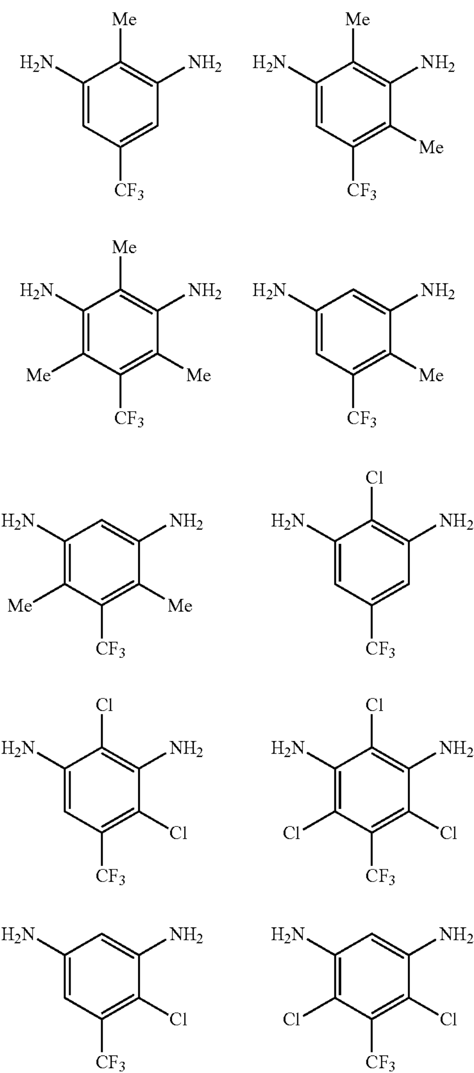

-continued

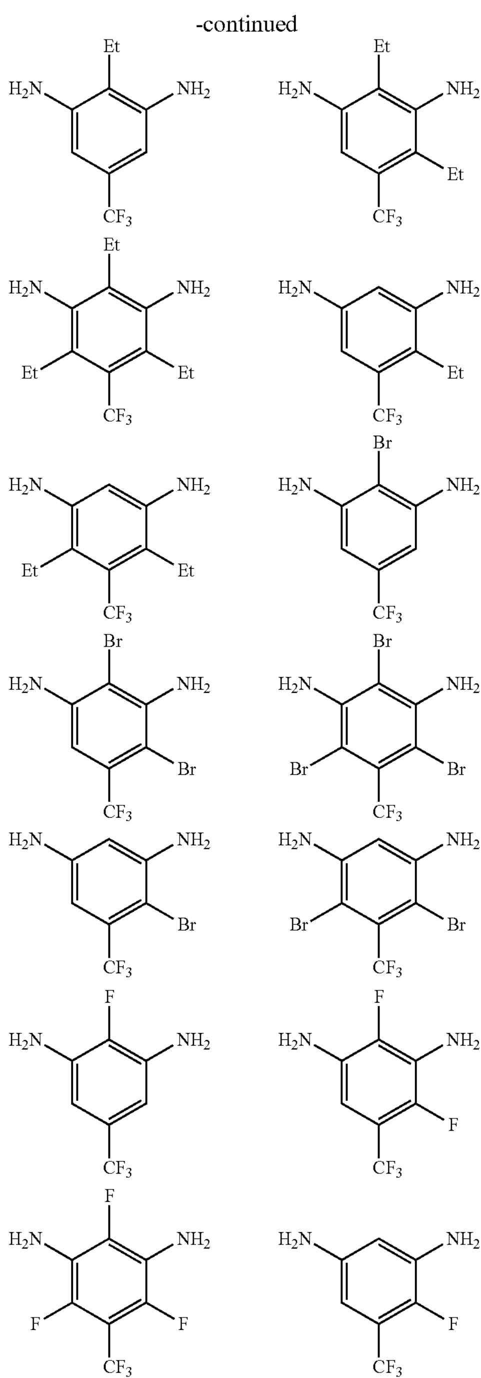

-continued
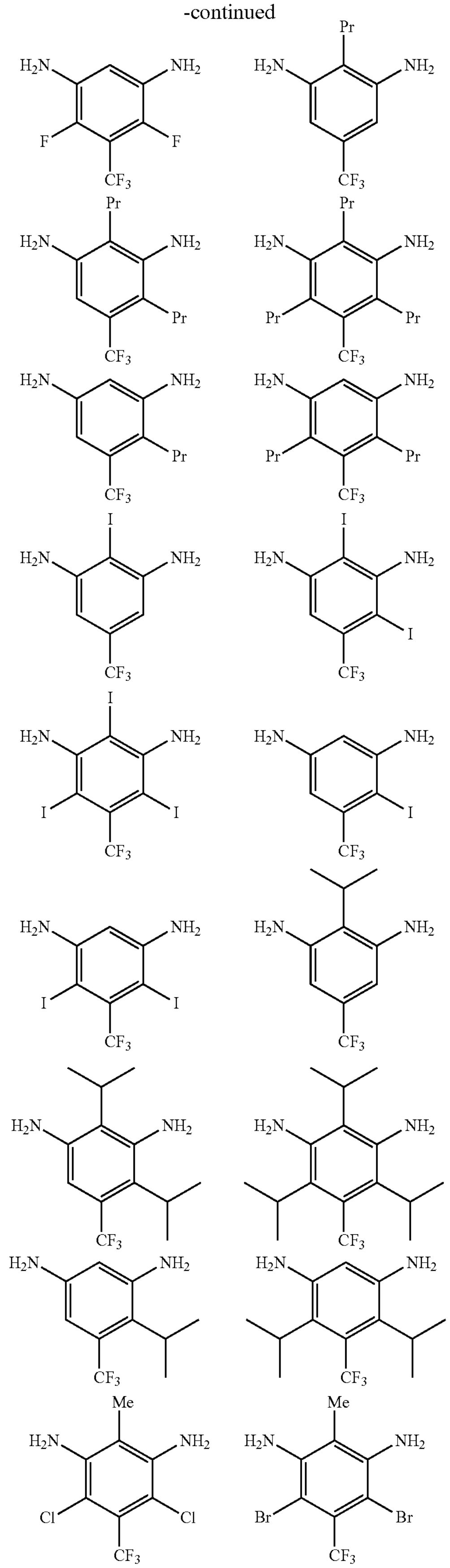
-continued
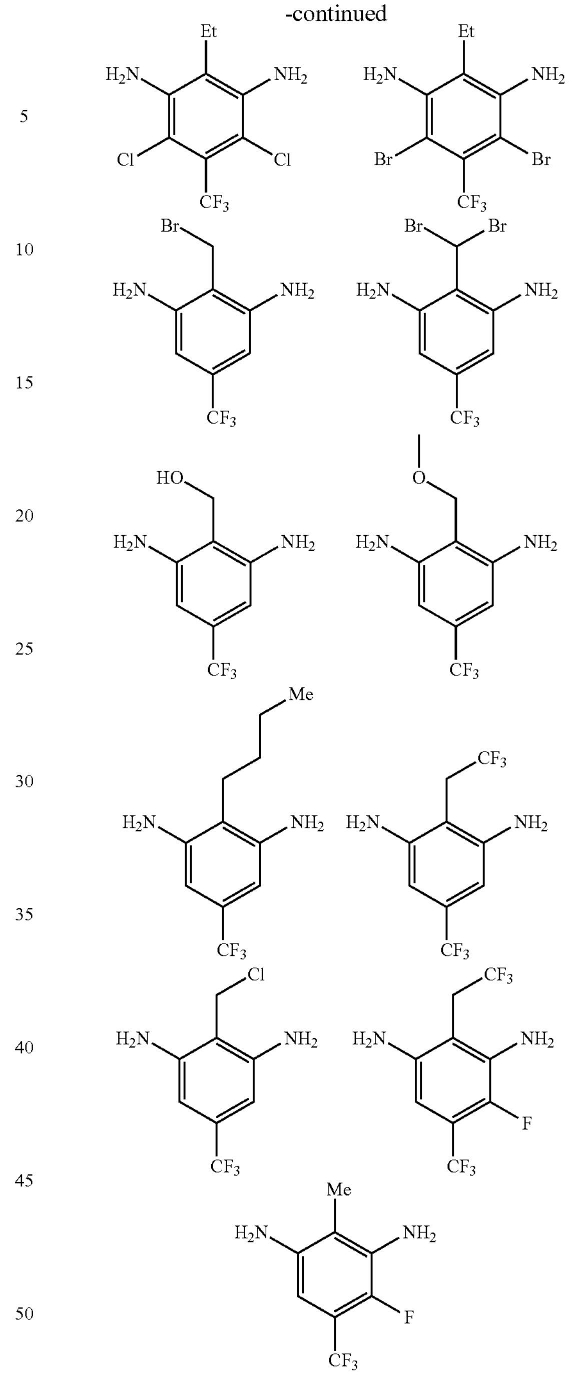
In the synthesis of the polyimide compound used in the present invention, a diamine compound represented by formula (IIIa) or formula (IVa) below may be used as the diamine compound serving as a raw material in addition to the diamine compound represented by the formula (Ia).
Formula (IIIa)
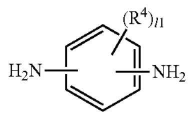

-continued

Formula (IVa)

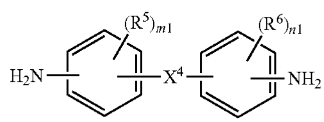

In the formula (IIIa), $R^4$ and 11 have the same meaning as $R^4$ and 11 in the formula (III), and the preferred forms are also the same. Herein, the diamine compound represented by the formula (IIIa) is not the diamine compound represented by the formula (Ia).

In the formula (IVa), $R^5$, $R^6$, $X^4$, m1, and n1 have the same meaning as $R^5$, $R^6$, $X^4$, m1, and n1 in the formula (IV), and the preferred forms are also the same.

Preferred specific examples of the diamine compound represented by the formula (IIIa) or (IVa) are shown below.

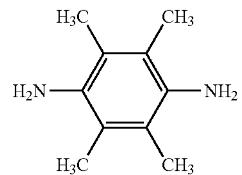

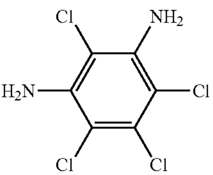

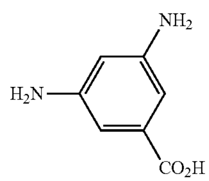

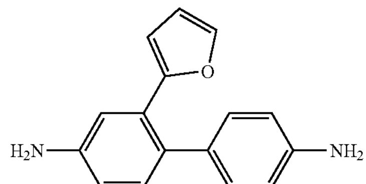

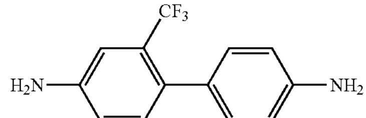

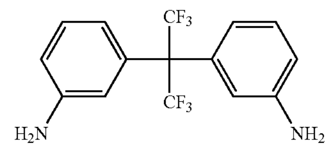

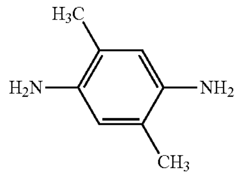

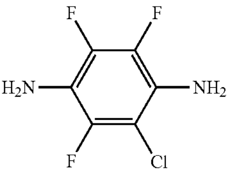

-continued

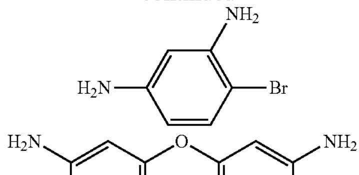

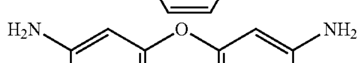

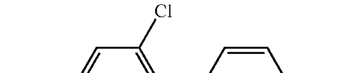

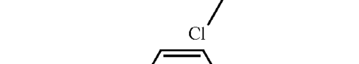

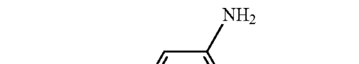

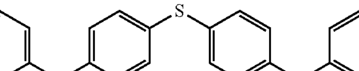

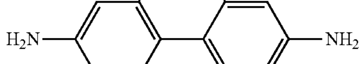

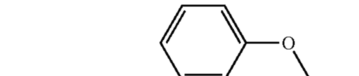

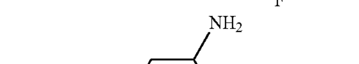

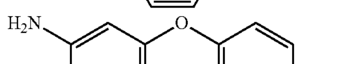

-continued
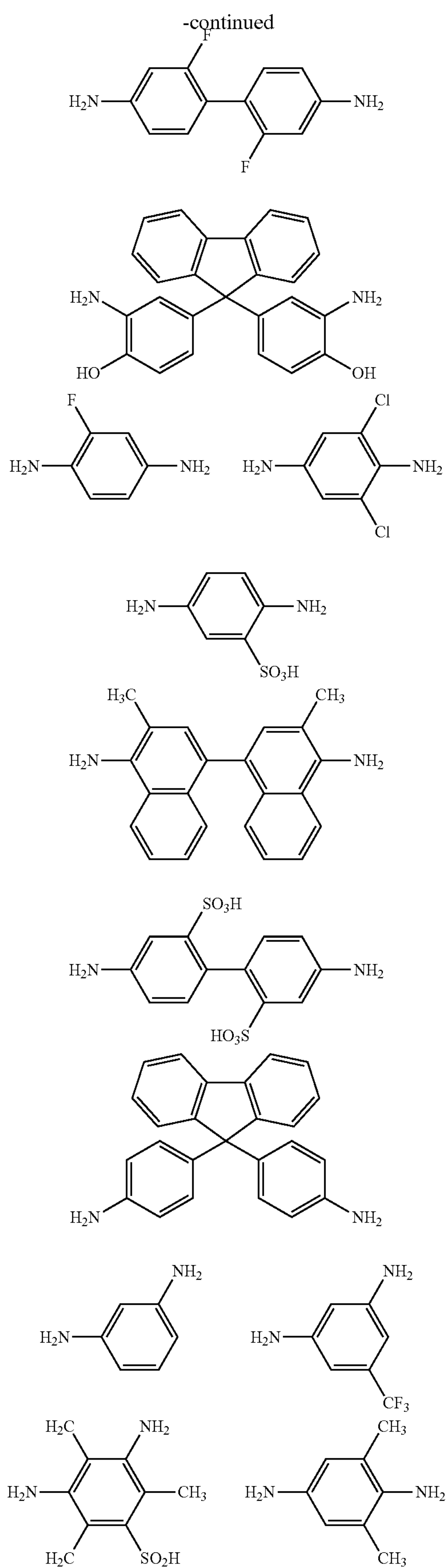
-continued
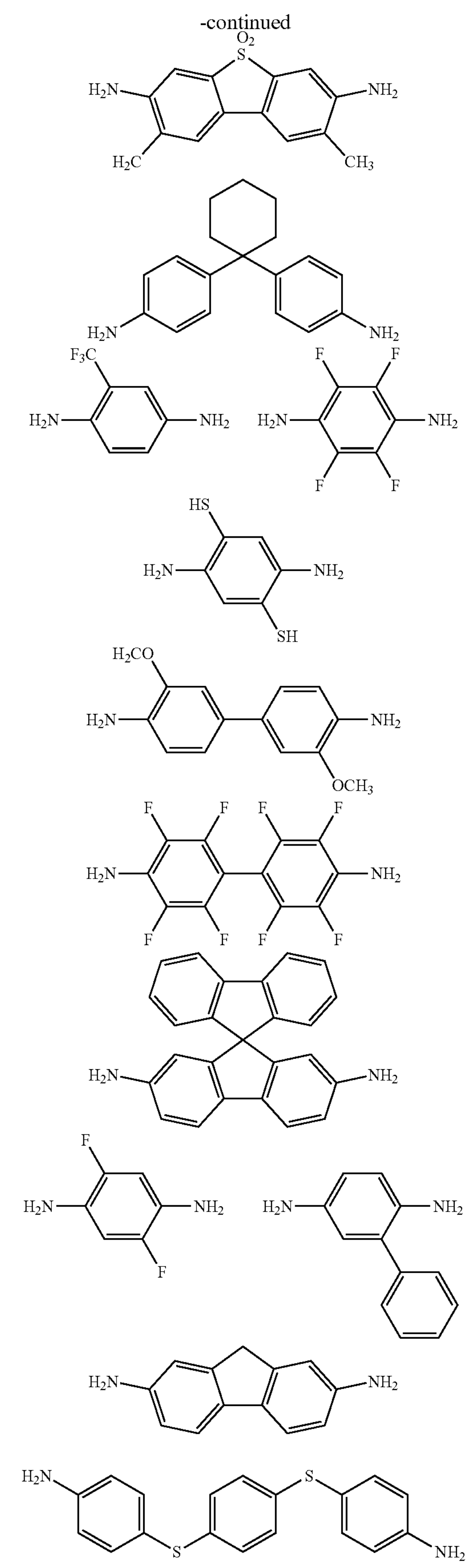

-continued
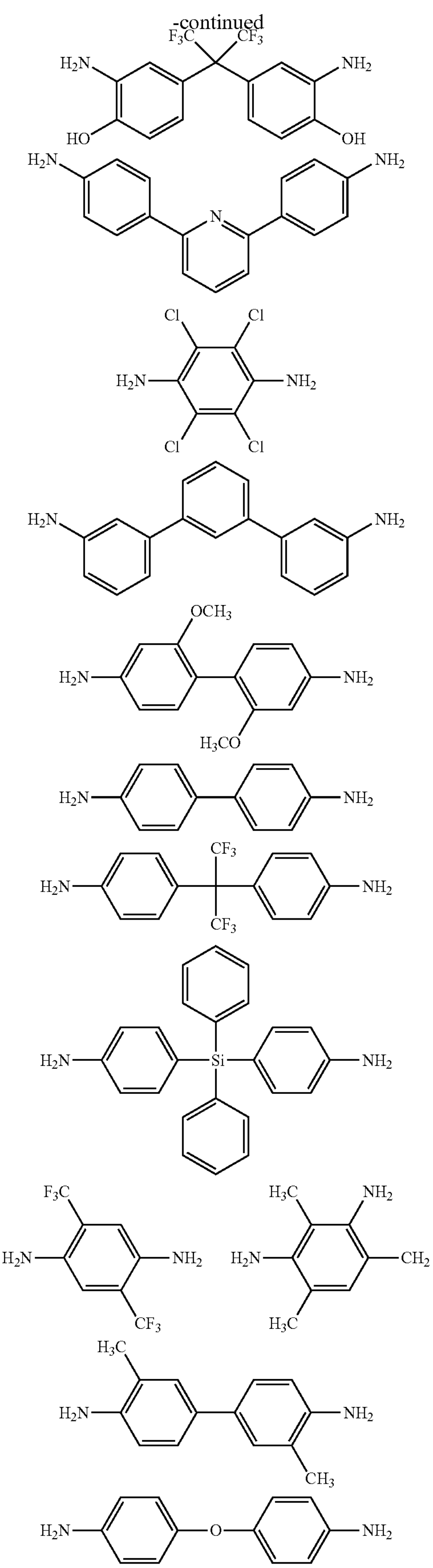
-continued
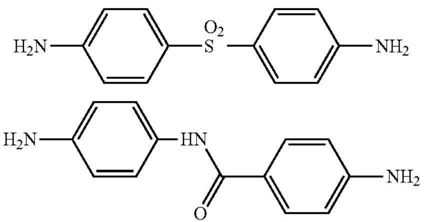
In the synthesis of the polyimide compound used in the present invention, a diamine compound that results in a repeating unit of polyiniides defined in paragraphs [0023] to [0034] of JP2015-83296A and paragraphs [0017] to [0045] of WO2017/002407A is also preferably used as the diamine compound serving as a raw material. Specific examples of the diamine compound are shown below.
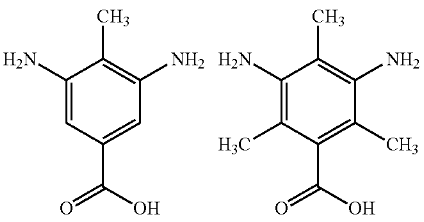
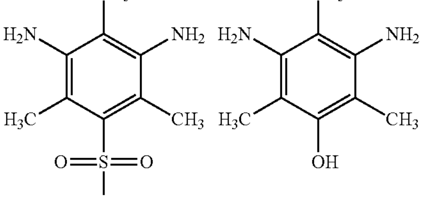
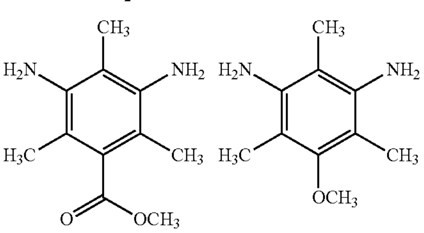
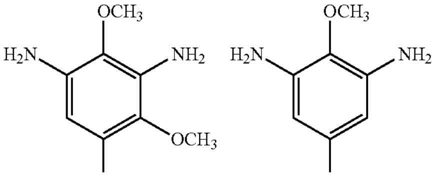
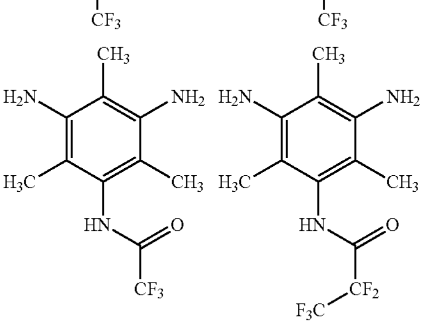

-continued

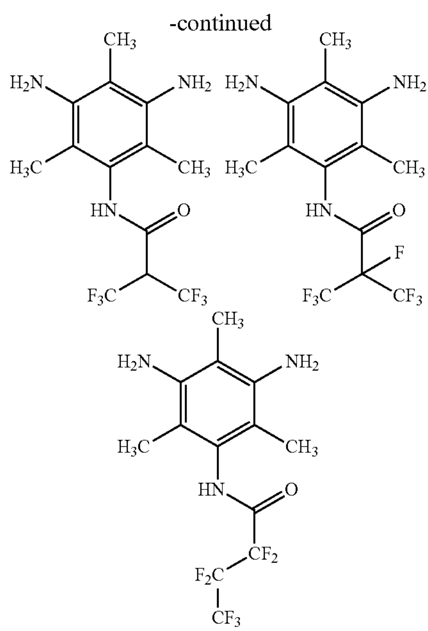

The polyimide compound used in the present invention may be any of block copolymers, random copolymers, and graft copolymers.

The polyimide compound used in the present invention can be obtained by mixing the above-described raw materials in a solvent and causing condensation polymerization by a typical method as described above.

Non-limiting examples of the solvent include ester compounds such as methyl acetate, ethyl acetate, and butyl acetate; aliphatic ketone compounds such as acetone, methyl ethyl ketone, methyl isobutyl ketone, di acetone alcohol, cyclopentanone, and cyclohexanone; ether compounds such as ethylene glycol dimethyl ether, dibutyl butyl ether, tetrahydrofuran, methylcyclopentyl ether, and dioxane; amide compounds such as N-methylpyrrolidone, 2-pyrrolidone, dimethylformamide, dimethylimidazolidinone, and dimethylacetamide; and sulfur-containing compounds such as dimethylsulfoxide and sulfolane. Such an organic solvent is appropriately selected so as to dissolve the tetracarboxylic dianhydride and diamine compound serving as reaction substrates, polyamic acid serving as a reaction intermediate, and a polyimide compound serving as an end product. The organic solvent is preferably an ester compound (preferably butyl acetate), an aliphatic ketone compound (preferably methyl ethyl ketone, methyl isobutyl ketone, diacetone alcohol, cvclopentanone, or cyclohexanone), an ether compound (diethylene glycol monomethyl ether, or methylcyclopentyl ether), an amide compound (preferably N-methylpyrrolidone), or a sulfur-containing compound (dimethylsulfoxide or sulfolane). These organic solvents may be used alone or in combination of two or more.

The polymerization reaction temperature is not particularly limited, and may be a temperature generally employed in the synthesis of polyimide compounds. Specifically, the polymerization reaction temperature is preferably −40° C. to 60° C. and more preferably −30° C. to 50° C.

The polyamic acid produced by the polymerization reaction is imidized through cyclodehydration in a molecule to obtain a polyimide compound. Examples of the imidization method that can be employed include a thermal imidization method of causing a reaction while performing heating in a range of 120° C. to 200° C. to remove water generated as a by-product to the outside of the system, and a so-called chemical imidization method in which a dehydration condensing agent such as acetic anhydride, dicyclohexylcarbodiimide, or triphenyl phosphite is used in the coexistence of a basic catalyst such as pyri dine, triethyl amine, or DBU.

In the present invention, the total concentration of the tetracarboxylic dianhydride and the diamine compound in a polymerization reaction liquid of the polyimide compound is not particularly limited, and is preferably 5 to 70 mass %, more preferably 5 to 50 mass %, and further preferably 5 to 30 mass %.

Next, the configuration of the gas separation membrane according to an embodiment of the present invention will be described. The gas separation membrane according to an embodiment of the present invention is provided to achieve an intended gas separation selectivity while ensuring gas permeability by thinning the gas separation layer. The method for thinning a gas separation layer is a method in which the gas separation membrane is formed into an asymmetric membrane by a phase separation process, and a portion that contributes to separation is formed as a thin layer referred to as a dense layer or a skin layer. In this asymmetric membrane, a portion other than the dense layer is allowed to function as a support layer that provides mechanical strength of the membrane.

A form of a composite membrane is also known in which a gas separation layer having a gas separation function and a support layer contributing to mechanical strength are separately provided, and the gas separation layer having a gas separation function is formed as a thin layer on the gas-permeable support layer. Each form will be described below in sequence.

Gas Separation Asymmetric Membrane

The gas separation asymmetric membrane can be formed by a phase inversion process using a solution including a polyimide compound. The phase inversion process is a publicly known process for forming a membrane while a polymer solution is brought into contact with a coagulating liquid to cause phase inversion. In the present invention, a so-called dry-wet process is suitably used. The dry-wet process includes evaporating a solution on a surface of a polymer solution with a membrane shape to form a thin dense layer, and subsequently immersing the dense layer in a coagulating liquid (a solvent which is compatible with a solvent of the polymer solution and in which the polymer is insoluble) to form a porous layer by forming fine pores using a phase-separation phenomenon that occurs at this time. This process was suggested by Loeb, Sourirajan, et al. (for example, U.S. Pat. No. 3,133,132A).

In the gas separation asymmetric membrane according to an embodiment of the present invention, the thickness of the surface layer that is referred to as a dense layer or a skin layer and contributes to gas separation is not particularly limited, and is preferably 0.01 to 5.0 μm and more preferably 0.05 to 1.0 μm from the viewpoint of imparting practical gas permeability. On the other hand, the porous layer located below the dense layer is configured to reduce the resistance to gas permeability and simultaneously impart mechanical strength. The thickness of the porous layer is not particularly limited as long as independent use of the asymmetric membrane is achieved. For example, the thickness can be set to 5 to 500 μm and is more preferably 5 to 200 μm and further preferably 5 to 100 μm.

The gas separation asymmetric membrane according to an embodiment of the present invention may be a flat membrane or a hollow fiber membrane. The asymmetric hollow fiber membrane can be produced by a dry-wet spinning process. The dry-wet spinning process is a process for producing an asymmetric hollow fiber membrane by applying a dry-wet process to a polymer solution that is ejected from a spinning nozzle to have a desired hollow fiber shape. More specifically, a polymer solution is ejected from a nozzle to have a desired hollow fiber shape and is allowed to pass through the air or a nitrogen gas atmosphere immediately after the ejection, and the resulting polymer solution is then immersed in a coagulating liquid which is compatible with a solvent of the polymer solution and in which the polymer is substantially insoluble to form an asymmetric structure. Subsequently, the asymmetric structure is dried and heat-treated, as needed, to produce a separation membrane.

The solution viscosity of the solution including the polyimide compound to be ejected from a nozzle is 2 to 17000 Pa·s, preferably 10 to 1500 Pa·s, and particularly preferably 20 to 1000 Pa·s at an ejection temperature (e.g., 10° C.) because the shape after ejection, such as a hollow fiber shape, can be stably obtained. It is preferable that immersion in the coagulating liquid be performed by immersing the ejected polymer solution in a primary coagulating liquid to be coagulated to such an extent that the shape of the membrane such as a hollow fiber shape can be maintained, then winding the resulting membrane around a guide roll, and subsequently immersing the membrane in a secondary coagulating liquid to sufficiently coagulate the whole membrane, The coagulated membrane is effectively dried after the coagulating liquid is substituted with a solvent such as a hydrocarbon. The heat treatment for drying is preferably performed at a temperature lower than the softening point or secondary transition point of the polyimide compound used.

Gas Separation Composite Membrane

In the gas separation composite membrane, a gas separation layer containing a particular polyimide compound is formed on the upper side of a gas permeable support layer. This composite membrane is preferably formed by applying a coating liquid (dope) for the above-described gas separation layer onto at least a top surface of a porous support (in this specification, "applying" includes adhesion on a surface by dipping).

Figure 2:
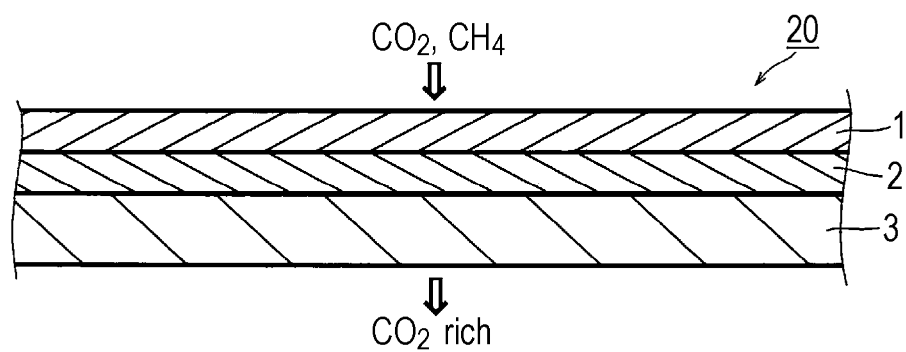
FIG. 2 is a sectional view schematically illustrating a gas separation composite membrane according to another embodiment of the present invention.

FIG. 1 is a longitudinal sectional view schematically illustrating a gas separation composite membrane 10 according to a preferred embodiment of the present invention. The reference numeral 1 denotes a gas separation layer, and the reference numeral 2 denotes a support layer formed of a porous layer. FIG. 2 is a sectional view schematically illustrating a gas separation composite membrane 20 according to a preferred embodiment of the present invention. In this embodiment, a nonwoven fabric layer 3 is added as a support layer in addition to the gas separation layer 1 and the porous layer 2.

FIGS. 1 and 2 illustrate a state in which carbon dioxide in a mixed gas of carbon dioxide and methane is allowed to selectively permeate the gas separation composite membrane.

In this specification, the "upper side of the support layer" means that another layer may be interposed between the support layer and the gas separation layer. For the expression of "upper and lower", the side to which a gas subjected to separation is supplied is an "upper side", and the side from which the separated gas is discharged is a "lower side" unless otherwise specified.

The gas separation composite membrane according to an embodiment of the present invention can be provided by forming a gas separation layer on at least a top surface of a porous support (support layer). The thickness of the gas separation layer is preferably as small as possible under the conditions that high gas permeability is imparted while mechanical strength and separation selectivity are maintained.

In the gas separation composite membrane according to an embodiment of the present invention, the thickness of the gas separation layer is not particularly limited, and is preferably 0.01 to 5.0 μm and more preferably 0.05 to 2.0 μm.

The porous support that is preferably applied to the support layer is not particularly limited as long as mechanical strength and high gas permeability are imparted, and may be formed of any of an organic material or an inorganic material. The porous support is preferably an organic high-molecular-weight porous membrane. The thickness is preferably 1 to 3000 μm, more preferably 5 to 500 μm, and further preferably 5 to 150 μm. For the pore structure of this porous membrane, the average pore diameter is normally 10 μm or less, preferably 0.5 μm or less, and more preferably 0.2 μm or less. The porosity is preferably 20 to 90% and more preferably 30 to 80%.

Herein, the phrase "the support layer has gas permeability" means that when carbon dioxide is supplied to the support layer (a membrane constituted by only the support layer) at 40° C. at a total pressure of 4 MPa on the gas supply side, the permeation rate of the carbon dioxide is $1\times10^{-5}$ $cm^3$ (STP)/$cm^2$·sec·cmHg (10 GPU) or more. For the gas permeability in the support layer, when carbon dioxide is supplied at 40° C. at a total pressure of 4 MPa on the gas supply side, the permeation rate of the carbon dioxide is preferably $3\times10^{-5}$ $cm^3$ (STP)/$cm^2$·sec·cmHg (30 GPU) or more, more preferably 100 GPU or more, and further preferably 200 GPU or more. Examples of the material for the porous membrane include publicly known polymers, e.g., polyolefin resins such as polyethylene and polypropylene, fluorine-containing resins such as polytetrafluoroethylene, polyvinyl fluoride, and polyvinylidene fluoride, and various resins such as polystyrene, cellulose acetate, polyurethane, polyacrylonitrile, polyphenylene oxide, polysulfone, polyethersulfone, polyimide, and polyaramide. The shape of the porous membrane may be, for example, any of a flat shape, a spiral shape, a tubular shape, and a hollow fiber shape.

In the gas separation composite membrane according to an embodiment of the present invention, a support for imparting mechanical strength is preferably further formed on the lower side of the support layer on which the gas separation layer is formed. Examples of the support include woven fabrics, nonwoven fabrics, and nets, and nonwoven fabrics are suitably used from the viewpoint of membrane formability and cost. As the nonwoven fabric, fibers formed of polyester, polypropylene, polyacrylonitrile, polyethylene, polyamide, or the like may be used alone or in combination of two or more. The nonwoven fabric can be produced by, for example, papermaking main fibers and binder fibers that are uniformly dispersed in water with a cylinder machine, a Fourdrinier machine, or the like and drying the resulting product with a dryer. Furthermore, for the purpose of, for example, removing fuzz or improving mechanical properties, the nonwoven fabric is also preferably subjected to a thermal pressing process while being interposed between two rolls.

The production method itself of the gas separation composite membrane is publicly known. For example, refer to JP2015-83296A.

In the gas separation membrane according to an embodiment of the present invention, the content of the polymer according to an embodiment of the present invention in the gas separation layer is not particularly limited as long as desired gas separation performance is achieved. From the viewpoint of further improving the gas separation performance, the content of the polymer according to an embodiment of the present invention in the gas separation layer is preferably 20 mass % or more, more preferably 40 mass % or more, more preferably 60 mass % or more, and further preferably 70 mass % or more. The content of the polymer according to an embodiment of the present invention in the gas separation layer may be 100 mass %, but is normally 99 mass % or less.

Another Layer Between Support Layer and Gas Separation Layer

In the gas separation composite membrane according to an embodiment of the present invention, another layer may be present between the support layer and the gas separation layer. A preferred example of the other layer is a siloxane compound layer. By disposing the siloxane compound layer, the irregularities on the uppermost surface of the support can be smoothened, which makes it easy to thin the separation layer. Examples of the siloxane compound for forming the siloxane compound layer include compounds whose main chain is constituted by polysiloxane and compounds having a siloxane structure and a non-siloxane structure in their main chains. Suitable examples of the siloxane compound layers include those described in paragraphs [0103] to [0127] in JP2015-160167A.

Protective Layer on Upper Side of Gas Separation Layer

The gas separation membrane may have, as a protective layer, a siloxane compound layer on the gas separation layer.

Suitable examples of the siloxane compound layer used as a protective layer include those described in paragraphs [0125] to [0175] in WO2017/002407A.

The gas separation membrane according to an embodiment of the present invention is preferably in the form of gas separation composite membrane.

Applications of Gas Separation Membrane

The gas separation membrane (composite membrane and asymmetric membrane) according to an embodiment of the present invention can be suitably used for gas separation recovery and gas separation purification. For example, a gas separation membrane can be provided that is capable of efficiently separating a particular gas in a gas mixture containing gases such as hydrogen, helium, carbon monoxide, carbon dioxide, hydrogen sulfide, oxygen, nitrogen, ammonia, sulfur oxides, nitrogen oxides, hydrocarbons, e.g., methane and ethane, unsaturated hydrocarbons, e.g., propylene, and perfluoro compounds, e.g., tetrafluoroethane. In particular, a gas separation membrane that selectively separates carbon dioxide in a gas mixture containing carbon dioxide/hydrocarbon (methane) is preferably provided.

The pressure during gas separation with the gas separation membrane according to an embodiment of the present invention is preferably 0.5 to 10 MPa, more preferably 1 to 10 MPa, and further preferably 2 to 7 MPa. The gas separation temperature is preferably −30° C. to 90° C. and more preferably 15° C. to 70° C.

Gas Separation Module and Gas Separation Apparatus

A gas separation membrane module can be provided by using the gas separation membrane according to an embodiment of the present invention. The module is, for example, a spiral-type module, a hollow fiber-type module, a pleated module, a tubular module, and a plate and frame-type module.

Furthermore, a gas separation apparatus having means for performing separation and recovery of gas or performing separation and purification of gas can be obtained by using the gas separation membrane or the gas separation module according to an embodiment of the present invention.

m-Phenylenediamine Compound

The m-phenylenediamine compound according to an embodiment of the present invention is represented by formula (Ia-1) below.

Formula (Ia-1)

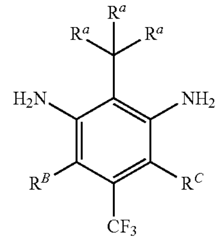

In the formula (Ia-1), $R^a$ represents a hydrogen atom, an alkyl group having 1 to 3 carbon atoms, a halogen atom, a hydroxy group, an alkoxy group having 1 to 3 carbon atoms, or an acyloxy group having 1 to 3 carbon atoms.

Herein, the number of carbon atoms of —$C(R^a)_3$ that bonds to the benzene ring in the formula (Ia-1) is 1 to 4 and preferably 1 to 3. Furthermore, —$C(R^a)_3$ is not trifluoromethyl (at least one of three $R^a$ is not a fluorine atom).

When —$C(R^a)_3$ is a substituted alkyl group as a whole, the substituent in this substituted alkyl group is a halogen atom, a hydroxy group, an alkoxy group having 1 to 3 carbon atoms, or an acyloxy group having 1 to 3 carbon atoms and is preferably a halogen atom.

In the formula (Ia-1), —$C(R^a)_3$ is preferably an unsubstituted alkyl group, more preferably unsubstituted ethyl or unsubstituted methyl, and further preferably unsubstituted methyl.

The halogen atom that may be represented by $R^a$ has the same meaning as the halogen atom that may be represented by $R^A$ in the formula (Ia), and the preferred form is also the same.

At least two $R^a$ in —$C(R^a)_3$ are also preferably hydrogen atoms.

$R_3$ and $R^C$ in the formula (Ia-1) have the same meaning as $R^B$ and $R^C$ in the formula (Ia), and the preferred forms are also the same.

Specific examples of the m-phenylenediamine compound according to an embodiment of the present invention are shown below.

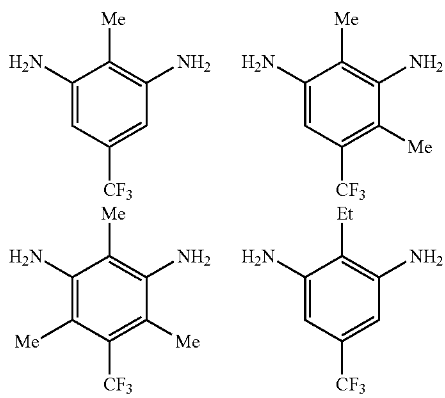

-continued

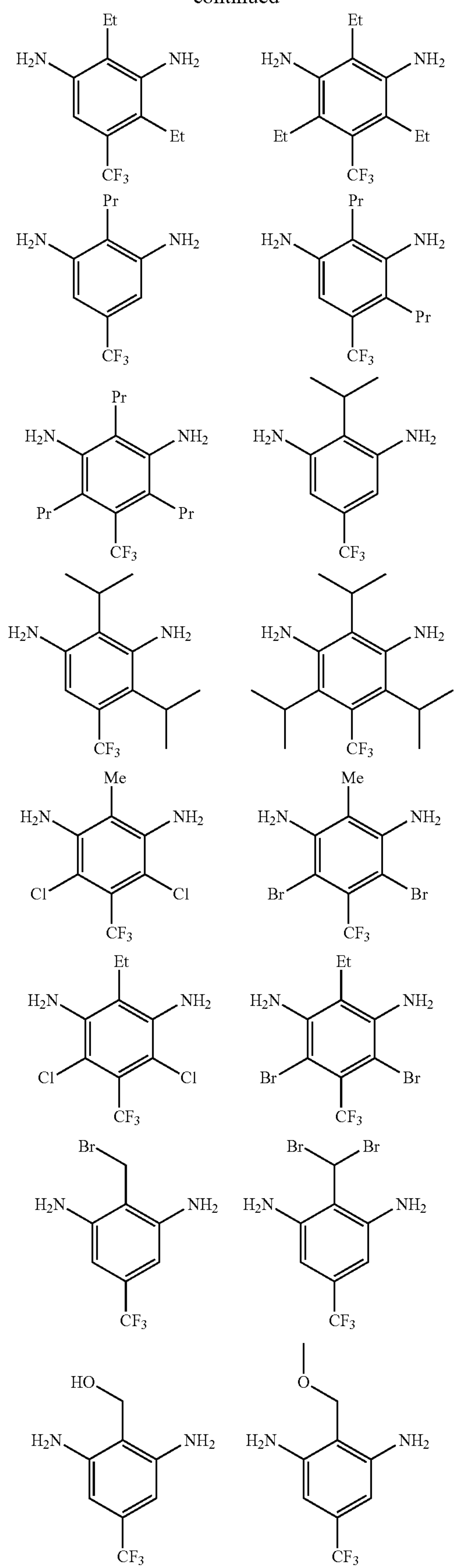

-continued

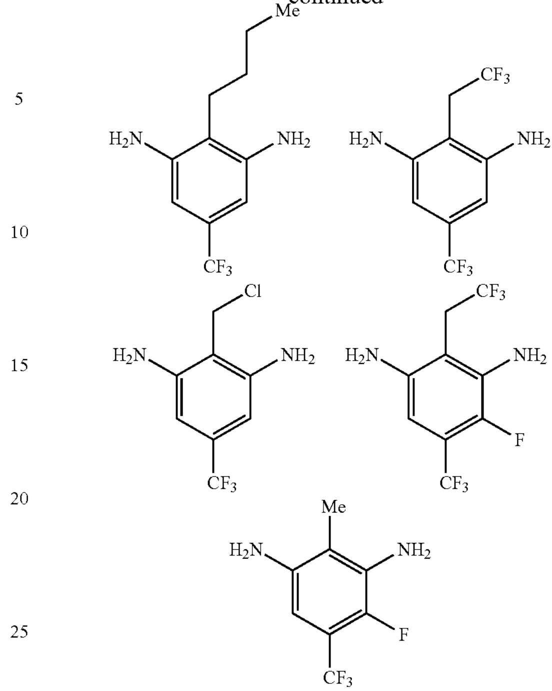

The method for obtaining the m-phenylenediamine compound according to an embodiment of the present invention is not particularly limited. For example, the m-phenylenediamine compound represented by the formula (Ia-1) can be prepared with reference to the preparation method described in Examples below or appropriately with reference to, for example, Chemistry Letters 1981, Vol. 10, No. 12; Ange. Chem. Int. Ed. 2011, 50, 3793-3798; Synthetic Communications, 22(22), 3189-3195, 1992; or Synthesis, (16), 2716-2726, 2004.

The m-phenylenediamine compound according to an embodiment of the present invention is suitably used as a raw material for synthesizing the polymer, and can impart desired characteristics to the polymer obtained. For example, the polymer obtained by using the m-phenylenediamine compound according to an embodiment of the present invention as a synthesis raw material (monomer) is allowed to have a low dielectric constant and higher transparency. The reason for this is unclear, but is probably as follows. The trifluoromethyl group positioned at a particular site of a constituent component derived from the m-phenylenediamine compound according to an embodiment of the present invention incorporated in the polymer contributes to reduction in dielectric constant and improvement in transparency of the polymer. Furthermore, a particular substituent of the constituent component suppresses, to some degree, the planarity or packing property of the polymer to appropriately form cavities in the polymer, which effectively contributes to reduction in dielectric constant and improvement in transparency.

Therefore, by using the m-phenylenediamine compound according to an embodiment of the present invention as a raw material for synthesizing various functional polymers, polymers for, for example, transparent heat-resistant resins, low dielectric constant resins, materials for high frequency, and moistureproof coating materials can be provided.

Furthermore, by using the m-phenylenediamine compound according to an embodiment of the present invention as a synthesis raw material, polymers suitable as materials for the gas separation layer of the gas separation membrane can be provided as described above.

By using the m-phenylenediamine compound according to an embodiment of the present invention as a synthesis raw material, a polyimide compound, a polyurethane compound, a polyurea compound, or a polyamide compound can be provided.

EXAMPLES

The present invention will be further described in detail based on Examples, but the present invention is not limited to Examples.

Synthesis Example 1

Preparation of Polyimide: P-01

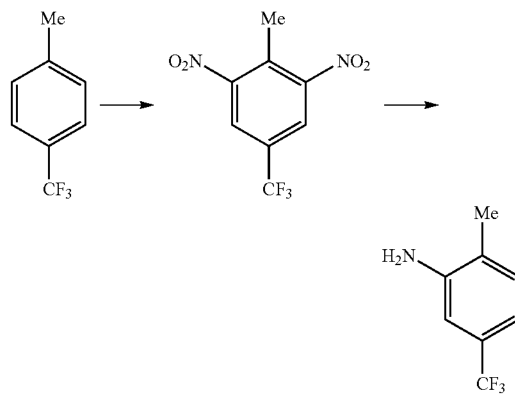

As described below, a diamine compound was prepared through the above scheme.

Into a three-necked flask, 23.3 g of 4-methylbenzotrifluoride (manufactured by Tokyo Chemical industry Co., Ltd.) was inserted, and cooled in an ice bath. After 87 mL of concentrated sulfuric acid (1.84 g/cm$^3$, manufactured by FUJIFILM Wako Pure Chemical Corporation) was added thereto, 46.4 g of fuming nitric acid (1.52 g/cm$^3$, manufactured by FUJIFILM Wako Pure Chemical Corporation) was carefully added dropwise thereto. The reaction was caused to proceed at an internal temperature of 50° C. for 3 hours, and the reaction product was then cooled with ice and carefully poured into ice. After filtration was carefully performed so that the target material was not dried, washing was performed with water and a saturated sodium bicarbonate solution to obtain 45 g of a dinitro compound including water.

Forty-five grams of the dinitro compound was dissolved in 400 mL of methanol, and inserted into a 1 L autoclave. After 7.3 g of palladium-activated carbon (Pd 5%) (manufactured by FUJIFILM Wako Pure Chemical Corporation) was inserted and the autoclave was hermetically sealed, the autoclave was filled with hydrogen at about 5 MPa and the reaction was caused to proceed at 30° C. for 6 hours. Filtration was carefully performed so that the palladium-activated carbon was not dried. The filtrate was concentrated under reduced pressure. Subsequently, the resulting solid was recrystallized with ethyl acetate and hexane. The resulting crystal was vacuum-dried at 80° C. for 8 hours to obtain 18.6 g of an intended diamine compound. The yield was 67% with respect to the 4-methylbenzotrifluoride.

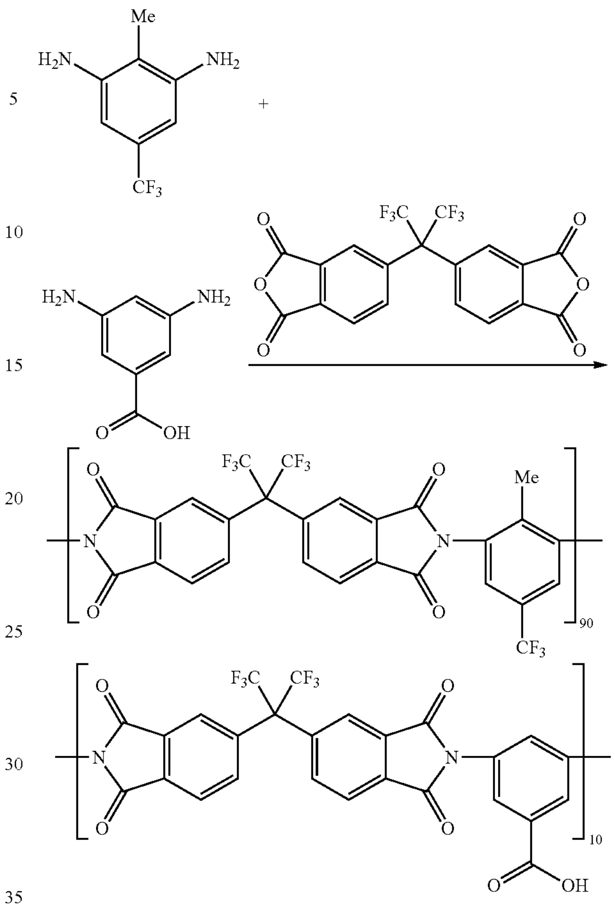

As described below, a polyimide P-01 was prepared through the above scheme.

Into a three-necked flask, 13.7 g of the diamine compound prepared above, 1.2 g of 3,5-diaminobenzoic acid (manufactured by Nipponjunryo Chemicals Co., Ltd.), and 98 mL of N-methylpyrrolidone (manufactured by FUJIFILM Wako Pure Chemical Corporation) were inserted, and treated in a nitrogen stream. Under water cooling, 35.5 g of 4,4'-(hexafluoroisopropylidene)diphthalic anhydride (manufactured by DAIKIN Industries, Ltd.) was added thereto, and washing was performed with 35 mL of N-methylpyrrolidone. After stirring was performed at 40° C. for 3 hours, 32 mL of toluene (manufactured by FUJIFILM Wako Pure Chemical Corporation) was added, and stirring was performed at 170° C. for 6 hours. After cooling to room temperature, the resulting product was diluted with 30 mL of N-methylpyrrolidone and 350 mL of acetone and transferred to a 5 L three-necked flask. To the three-necked flask, 2 L of methanol was added dropwise to precipitate the polyimide in the form of white powder. Suction filtration, reslurry washing with methanol, and air blow drying at 50° C. for 20 hours were performed to obtain 40.3 g (yield 85%) of a polyimide P-01. The weight-average molecular weight measured by gel penneati on chromatography using tetrahydrofuran was 92000.

Preparation of Polyimides P-02 to P-11 and cP-01 to cP-03

Polyimides P-02 to P-11 and cP-01 to cP-03 were obtained in the same manner as in Preparation of polyimide P-01, except that the raw materials used were changed to those that lead to the following structures. All the polyimides had a weight-average molecular weight in the range of 30000 to 200000.

The structures of the polyimides P-01 to P-11 and cP-01 to cP-03 are shown below. In the following structures, the numerical values attached to constitutional units indicate a molar ratio (%).
P-01
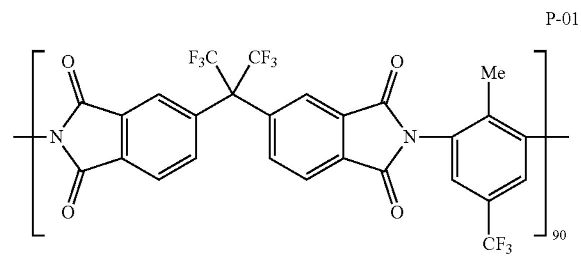
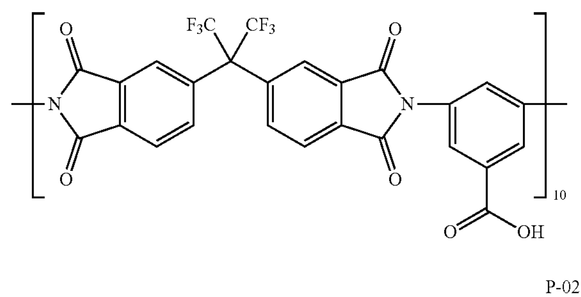
P-02
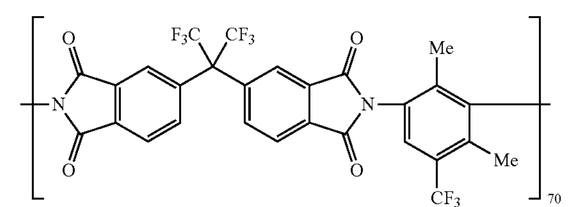
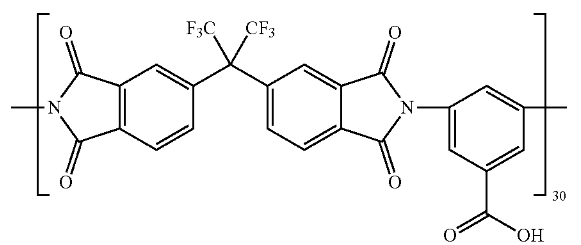
P-03
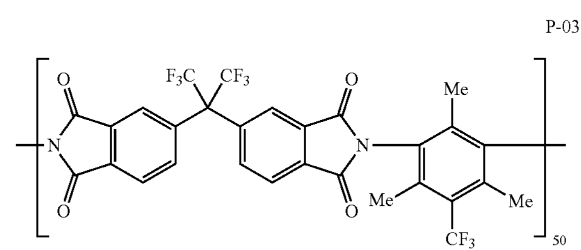
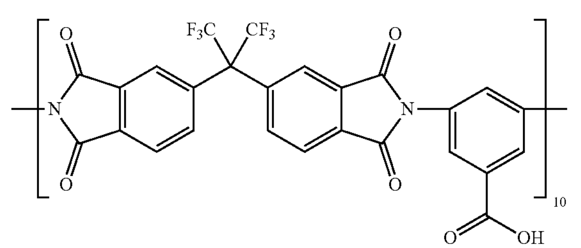
-continued
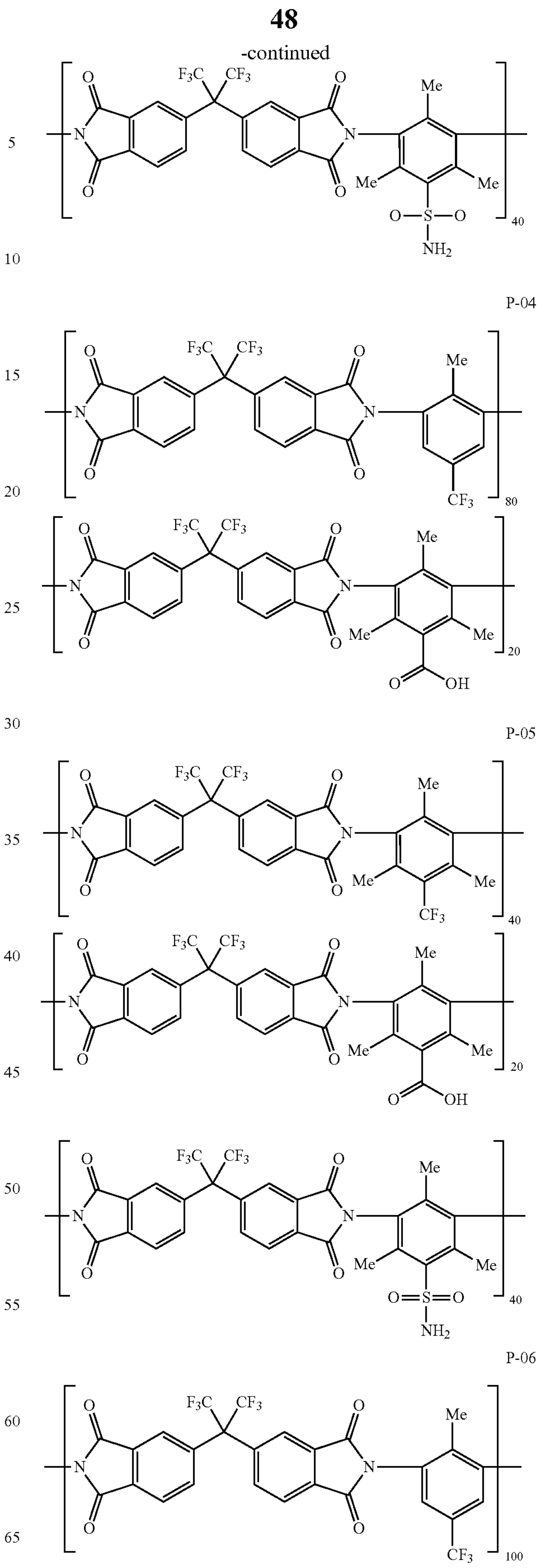

-continued

P-07

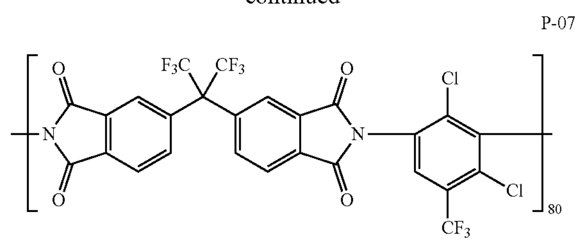

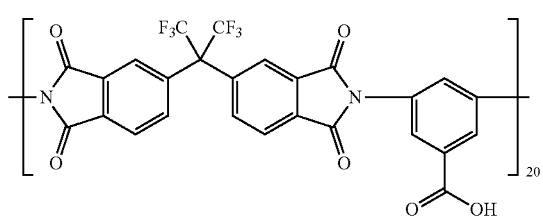

P-08

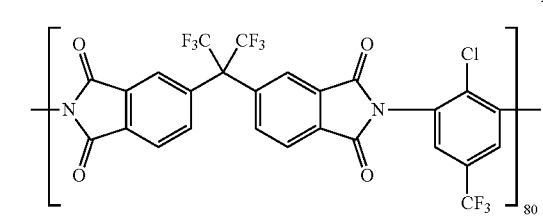

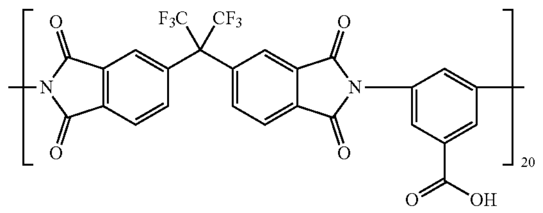

P-09

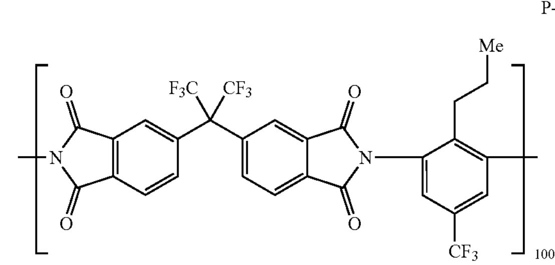

P-10

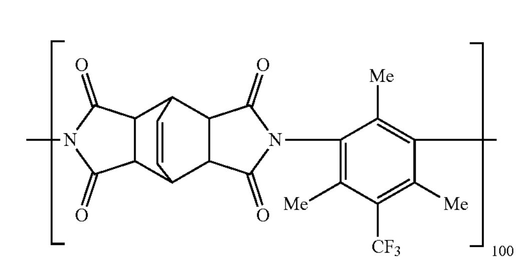

P-11

-continued

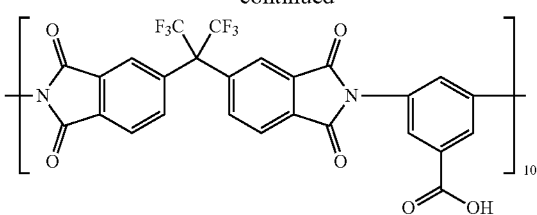

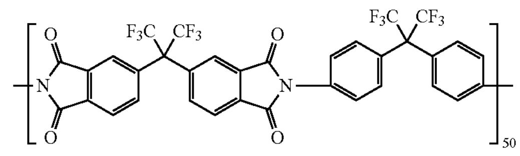

cP-01

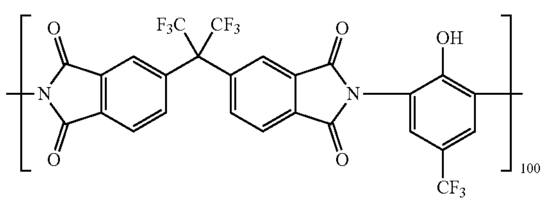

cP-02

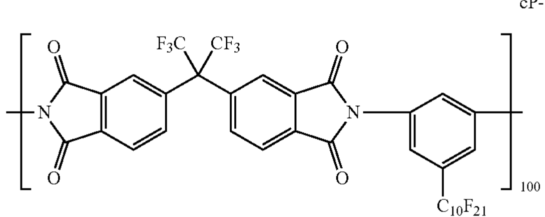

cP-03

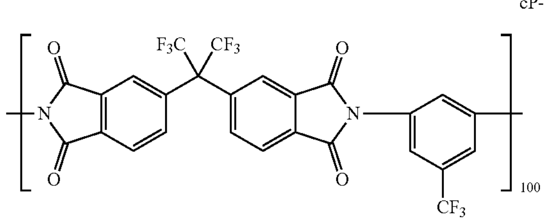

Preparation of Polyimides P-12 to P-19

Polyimides P-12 to P-19 were obtained in the same manner as in Preparation of polyimide P-01, except that the raw materials used were changed to those that lead to the following structures. All the polyimides had a weight-average molecular weight in the range of 30000 to 200000.

The structures of the polyimides P-12 to P-19 are shown below. In the following structures, the numerical values attached to constitutional units indicate a molar ratio (%).

P-12

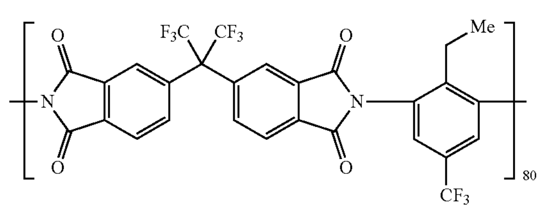

-continued
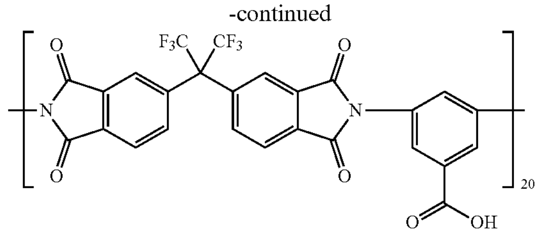
P-13
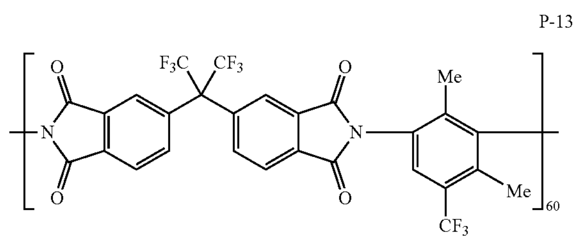
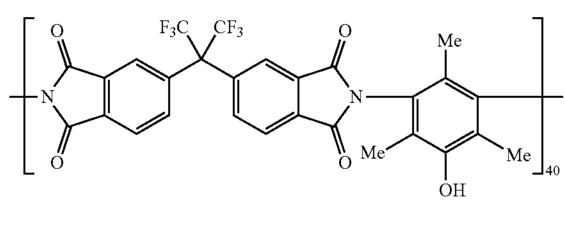
P-14
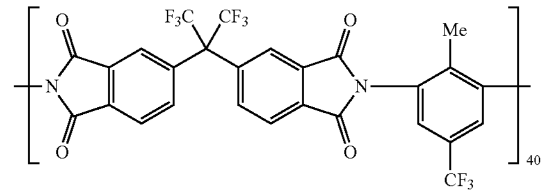
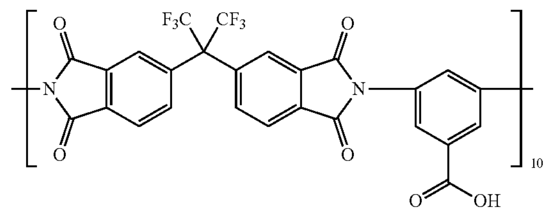
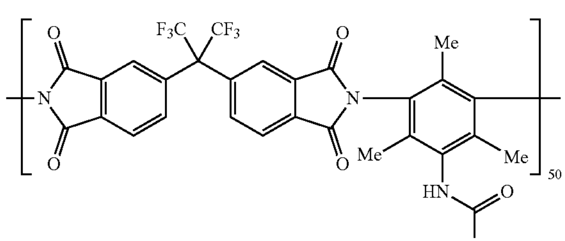
P-15
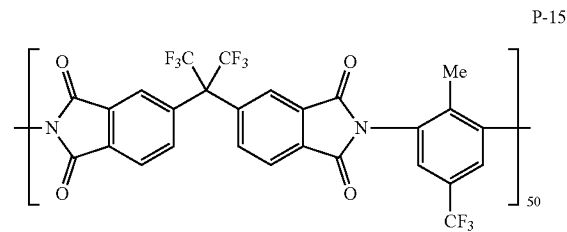
-continued
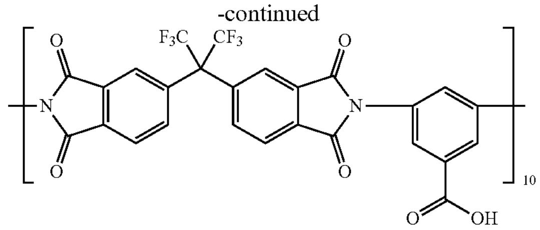
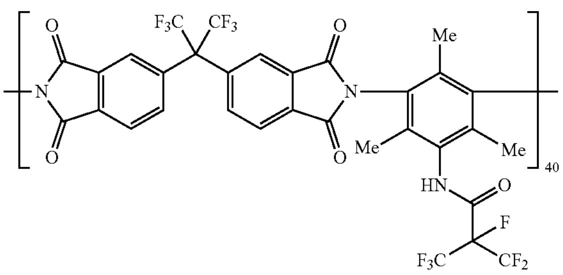
P-16
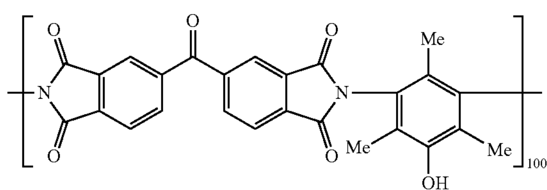
P-17
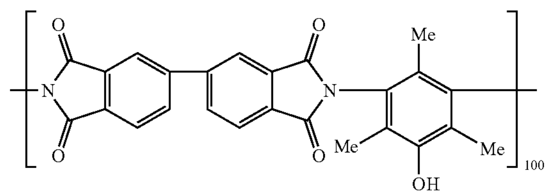
P-18
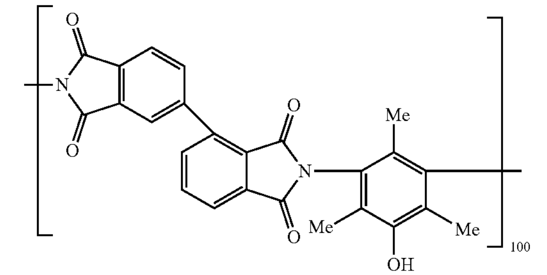
P-19
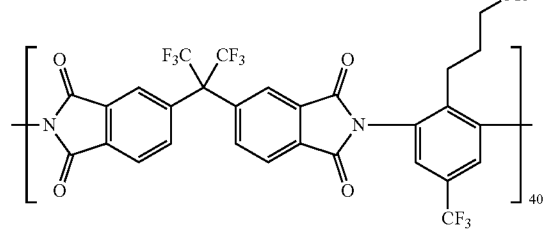

-continued

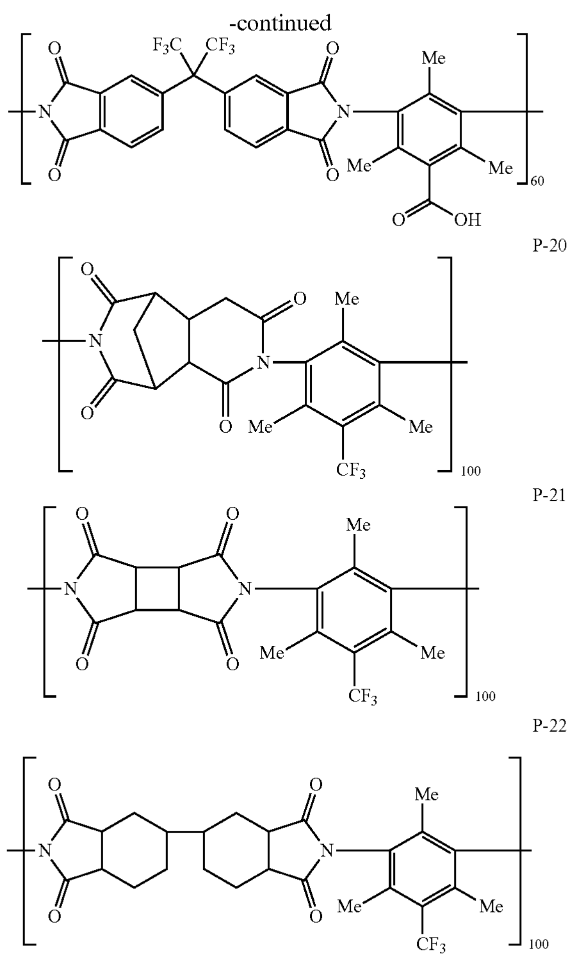

Example 1

Production of Gas Separation Membrane

Production of PAN Porous Membrane with Smooth Layer

Preparation of Radiation-Curable Polymer Having Dialkylsiloxane Group

Into a 150 mL three-necked flask, 39 g of UV9300 (manufactured by Momentive), 10 g of X-22-162C (manufactured by Shin-Etsu Chemical Co,, Ltd.), and 0.007 g of DBU (1,8-diazabicyclo[5.4.0]undec-7-ene) were inserted, and they were dissolved in 50 g of n-heptane. This was maintained at 95° C. for 168 hours to obtain a radiation-curable polymer solution having a poly(siloxane) group (viscosity 22.8 mPa·s at 25° C.).

Preparation of Polymerizable Radiation-Curable Composition

Five grams of the radiation-curable polymer solution was cooled to 20° C. and diluted with 95 g ofn-heptane. The resulting solution was mixed with 0.5 g of UV9380C (manufactured by Momentive) serving as a photopolymerization initiator and 0.1 g of ORGATIX TA-10 (manufactured by Matsumoto Fine Chemical Co., Ltd.) to prepare a polymerizable radiation-curable composition.

Application of Polymerizable Radiation-Curable Composition Onto Porous Support and Formation of Smooth Layer The polymerizable radiation-curable composition was subjected to spin coating on a polyacrylonitrile (PAN) porous membrane (a polyacrylonitrile porous membrane was present on a nonwoven fabric, and the thickness of the polyacrylonitrile porous membrane including the nonwoven fabric was about 180 μm) serving as a support. Subsequently, UV treatment (manufactured by Fusion UV Systems, Light Hammer 10, D-bulb) was performed at a UV intensity of 24 kW/m for a treatment time of 10 seconds, and then drying was performed. Thus, a smooth layer having a dialkylsiloxane group and a thickness of 1 μm was formed on the porous support.

Production of Gas Separation Membrane

A gas separation composite membrane illustrated in FIG. 2 was produced (FIG. 2 does not illustrate a smooth layer).

In a 30 ml brown vial, 0.08 g of the polyimide P-01 and 7.92 g of tetrahydrofuran were mixed with each other and stirred for 30 minutes. Subsequently, the resulting mixture was subjected to spin coating on the PAN porous membrane with the smooth layer to form a gas separation layer, thereby obtaining a composite membrane, The polyimide P-01 layer had a thickness of about 100 nm, and the PAN porous membrane including the nonwoven fabric had a thickness of about 180 μm.

The polyacrylonitrile porous membrane used was a membrane having a molecular weight cutoff of 100,000 or less. The permeability of the porous membrane for carbon dioxide at 40° C. and 5 MPa was 25000 GPU.

Examples 2 to 19

Production of Gas Separation Membrane

Gas separation membranes in Examples 2 to 19 were produced in the same manner as in Example 1, except that the polyimide P-01 was changed to the polyimides P-02 to P-19 in the production of the composite membrane in Example 1.

Comparative Examples 1 to 3

Production of Gas Separation Membrane

Gas separation membranes in Comparative Examples 1 to 3 were produced in the same manner as in Example 1, except that the polyimide P-01 in Example 1 was changed to the polyimides cP-01 to cP-03.

Test Example 1

Evaluation of $CO_2$ Permeation Rate and Gas Separation Selectivity of Gas Separation Membrane-1

The gas separation performance was evaluated as follows using the gas separation membranes (composite membranes) in Examples and Comparative Examples.

The gas separation membrane was cut off together with the porous support (support layer) so as to have a diameter of 47 mm. Thus, a permeation test sample was produced. With a gas permeation analysis system manufactured by GTR TEC Corporation, a mixed gas having a volume ratio of carbon dioxide ($CO_2$):methane ($CH_4$)=10:90 was supplied while the total pressure on the gas supply side was adjusted to 5 MPa (partial pressure of $CO_2$: 0.3 MPa), the flow rate was adjusted to 500 mL/min, and the temperature was adjusted to 45° C. The permeated gas was analyzed by gas chromatography. The gas permeability of the membrane was determined by calculating the $CO_2$ permeation rate as a gas permeance. The gas permeance (gas permeation rate) was expressed in units of GPU [1 GPU=$1\times10^{-6}$ $cm^3$ (STP)/$cm^2$·sec·cmHg]. The gas separation selectivity was calculated as a ratio ($R_{CO2}/R_{CH4}$) of $CO_2$ permeation rate $R_{CO2}$ to $CH_4$ permeation rate $R_{CH4}$ of the membrane.

The $CO_2$ permeation rate and the gas separation selectivity were applied to the following evaluation criteria to evaluate the performance of the gas separation membrane.

Evaluation Criteria of $CO_2$ Permeation Rate

A: 120 GPU or more

B: 105 GM or more and less than 120 GPU

C: 90 GPU or more and less than 105 GPU

D: 75 GPU or more and less than 90 GPU

E: less than 75 GPU

Evaluation Criteria of Gas Separation Selectivity ($R_{CO2}/R_{CH4}$)

A: 18 or more

B: 14 or more and less than 18

C: 10 or more and less than 14

D: less than 10

Test Example 2

Forced Drying Test

The gas separation membrane (composite membrane) in each of Examples and Comparative Examples was left to stand at 90° C. for 2 weeks for drying. The $CO_2$ permeation rate was determined in the same manner as in Test Example 1 using the dried gas separation membrane. The evaluation criteria of the $CO_2$ permeation rate were the same as those in Test Example 1 From this test, the applicability to, for example, a natural gas field with a small amount of plasticizing component can be evaluated in a simulated manner.

Table 1 below shows the results in each of Test Examples.

TABLE 1

| | | Test Example 1 | | Test Example 2 |
|---|---|---|---|---|
| | Polymer | $CO_2$ permeation rate | $R_{CO2}/R_{CH4}$ | $CO_2$ permeation rate |
| Example 1 | P-01 | A | A | A |
| Example 2 | P-02 | A | A | A |
| Example 3 | P-03 | A | A | A |
| Example 4 | P-04 | A | A | A |
| Example 5 | P-05 | A | A | A |
| Example 6 | P-06 | A | A | A |
| Example 7 | P-07 | A | B | A |
| Example 8 | P-08 | B | A | B |
| Example 9 | P-09 | A | B | A |
| Example 10 | P-10 | B | B | B |
| Example 11 | P-11 | B | A | B |
| Comparative Example 1 | cP-01 | C | A | D |
| Comparative Example 2 | cP-02 | A | D | B |
| Comparative Example 3 | cP-03 | D | A | E |
| Example 12 | P-12 | A | A | A |
| Example 13 | P-13 | A | A | A |
| Example 14 | P-14 | A | B | A |
| Example 15 | P-15 | A | B | A |
| Example 16 | P-16 | B | A | B |
| Example 17 | P-17 | B | A | B |
| Example 18 | P-18 | B | A | B |
| Example 19 | P-19 | A | B | A |
| Example 20 | P-20 | B | B | B |
| Example 21 | P-21 | B | B | B |
| Example 22 | P-22 | B | B | B |

As shown in Table 1, when the diamine component of the polymer had a phenylene structure having perfluoromethyl as specified in the present invention, but did not have a particular substituent specified in the present invention, the gas separation membrane having a gas separation layer formed of this polymer had a poor gas permeation rate, which was further decreased after exposed to dry conditions (Comparative Examples 1 and 3). Furthermore, when a long-chain perfluoroalkyl group was introduced to the diamine component of the polymer instead of the perfluoromethyl, the gas separation selectivity was considerably deteriorated (Comparative Example 2).

In contrast, the gas separation membrane using, as a gas separation layer, the polymer having the diamine component having a structure specified in the present invention had both high gas permeation rate and high gas separation selectivity. Even when the gas separation membrane was exposed to dry conditions, a sufficient gas permeation rate could be maintained (Examples 1 to 19).

Synthesis Example 2

Preparation of Polyamide PA-01

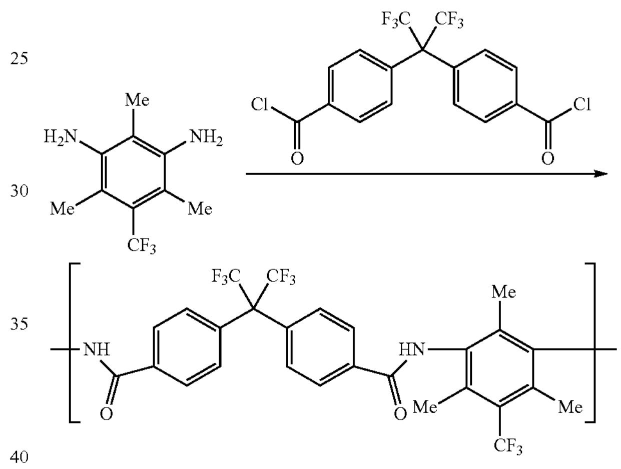

A polyamide PA-01 was prepared as follows through the above scheme.

After 2.00 g of 4,4'-(hexafluoroisopropylidene)bis(benzoic acid) dichloride (synthesized by a typical method), 1.02 g of a diamine (synthesized as above), 20 g of N-methylpyrrolidone (manufactured by FUJIFILM Wako Pure Chemical Corporation), and 1.20 g of 4-dimethylaminopyridine (manufactured by FUJIFILM Wako Pure Chemical Corporation) were inserted, they were stirred under heating at 60° C. for 4 hours. After cooling to room temperature, the concentration was adjusted using 10 g of N-methylpyrrolidone, and reprecipitation was caused using methanol to obtain 2.4 g of an intended polyamide PA-01. The weight-average molecular weight measured by gel permeation chromatography using N-methylpyrrolidone was 30000.

PA-01

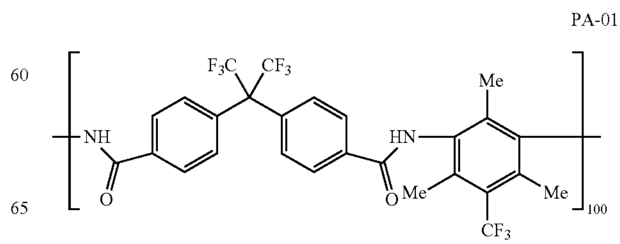

Preparation of Polyamides PA-02 and PA-03

Polyamides PA-02 and PA-03 below were prepared in the same manner as in Preparation of polyamide PA-01, except that the raw materials used were changed to those that lead to the following structures.

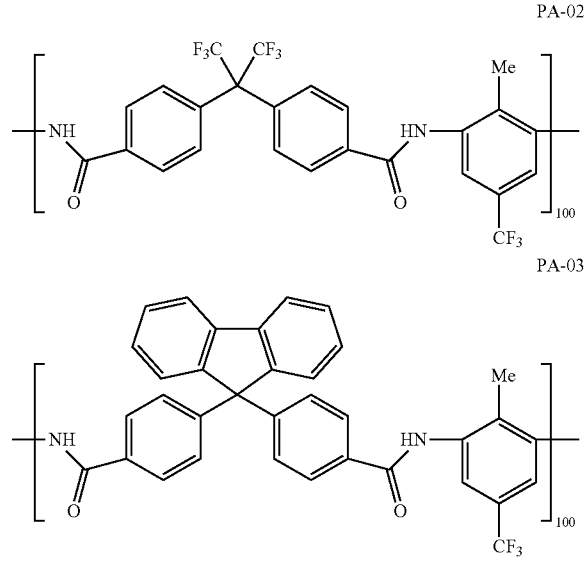

Synthesis Example 3

Preparation of Polyurea PU-01

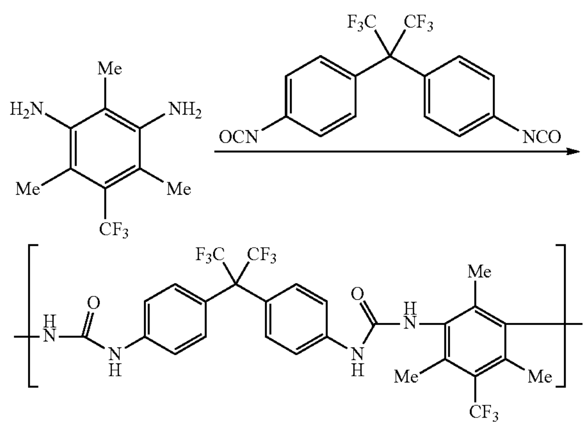

A polyurea PU-01 was prepared as follows through the above scheme.

After 1.00 g of 2,2-bis(4-isocyanatophenyl)hexafluoropropane (manufactured by Tokyo Chemical Industry Co., Ltd.), 0.56 g of a diamine (synthesized as above), 10 g of N-methylpyrrolidone (manufactured by FUJIFILM Wako Pure Chemical Corporation), and 0.05 g of NEOSTANN U-600 (manufactured by Nitto Kasei Co., Ltd.) were inserted, they were stirred under heating at 70° C. for 6 hours. After cooling to room temperature, the concentration was adjusted using 10 g of N-methylpyrrolidone, and reprecipitation was caused using methanol to obtain 1.4 g of an intended polyurea PU-01. The weight-average molecular weight measured by gel permeation chromatography using N-methylpyrrolidone was 25000.

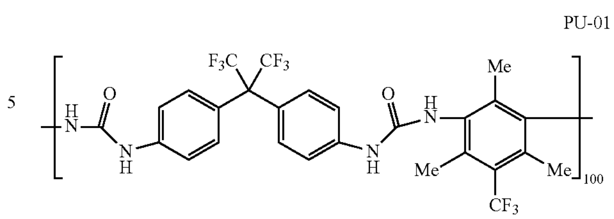

Synthesis example 4

Preparation of m-phenylenediamine Compound DA-1

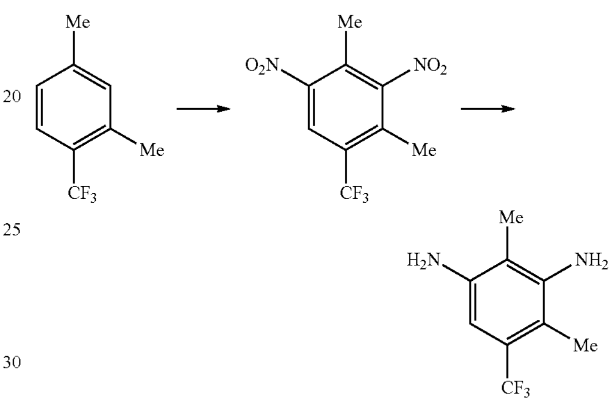

A m-phenylenediamine compound DA-1 was prepared as follows through the above scheme.

Into a three-necked flask, 4.5 g of 2,4-dimethylbenzotrifluoride (manufactured by Oakwood Products, Inc.) was inserted, and cooled in an ice bath. After 24 mL of concentrated sulfuric acid (1.84 g/cm3, manufactured by FUJIFILM Wako Pure Chemical Corporation) was added thereto, 9.7 g of fuming nitric acid (1.52 g/cm3, manufactured by FUJIFILM Wako Pure Chemical Corporation) was carefully added dropwise thereto. The reaction was caused to proceed at an internal temperature of 50° C. for 3 hours, and the reaction product was then cooled with ice and carefully poured into ice. After filtration was carefully performed so that the target material was not dried, washing was performed with water and a saturated sodium bicarbonate solution to obtain 10 g of a dinitro compound including water.

Ten grams of the dinitro compound was dissolved in 200 mL of methanol, and inserted into a 0.5 L autoclave. After 1.4 g of palladium-activated carbon (Pd 5%) (manufactured by FUJIFILM Wako Pure Chemical Corporation) was inserted and the autoclave was hermetically sealed, the autoclave was filled with hydrogen at about 5 MPa and the reaction was caused to proceed at 35° C. for 7 hours. Filtration was carefully performed so that the palladium-activated carbon was not dried. The filtrate was concentrated under reduced pressure. Subsequently, the resulting solid was purified through silica gel columns using ethyl acetate and chloroform. The resulting crystal was vacuum-dried at 60° C. for 8 hours to obtain 4.3 g of an intended m-phenylenediamine compound DA-1 (the compound on the right end of the above scheme). The yield was 82% with respect to the 2,4-dimethylbenzotrifluoride.

The spectrum data of the obtained m-phenylenediamine compound DA-1 is shown below.

$^{1}$H NMR (400 MHz, $CDCl_3$) δppm 6.51 (s, 1H), 3.72 (brs, 2H), 3.59 (brs, 2H (d, J=1.2 Hz, 3H), 2.02 (s, 3H), $^{19}$F NMR (376 MHz, $CDCl_3$) δppm −59.98 (s, 6F)

Preparation of m-phenylenediamine Compound DA-2

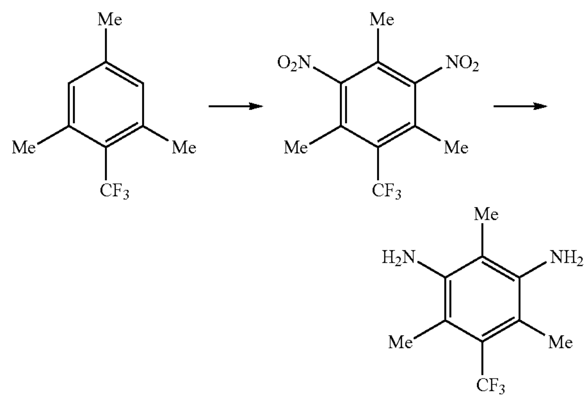

A m-phenylenediamine compound DA-2 was prepared as follows through the above scheme.

Into a three-necked flask, 1.6 g of 2,4,6-trimethylbenzotrifluoride (manufactured by Oakwood Products, Inc.) was inserted, and cooled in an ice bath. After 7.5 mL of concentrated sulfuric acid (1.84 g/cm3, manufactured by FUJIFILM Wako Pure Chemical Corporation) was added thereto, 4.0 g of fuming nitric acid 0.52 g/cm3, manufactured by FUJIFILM Wako Pure Chemical Corporation) was carefully added dropwise thereto. The reaction was caused to proceed at an internal temperature of 50° C. for 3 hours, and the reaction product was then cooled with ice and carefully poured into ice. After filtration was carefully performed so that the target material was not dried, washing was performed with water and a saturated sodium bicarbonate solution to obtain 4 g of a dinitro compound including water.

Four grams of the dinitro compound was dissolved in 80 mL of methanol, and inserted into a 0.2 L autoclave. After 0.5 g of palla.dium-activated carbon (Pd 5%) (manufactured by FUJIFILM Wako Pure Chemical Corporation) was inserted and the autoclave was hermetically sealed, the autoclave was filled with hydrogen at about 5 MPa and the reaction was caused to proceed at 30° C. for 6 hours. Filtration was carefully performed so that the palladium-activated carbon was not dried. The filtrate was concentrated under reduced pressure. Subsequently, the resulting solid was recrystallized with ethyl acetate and hexane. The resulting crystal was vacuum-dried at 80° C. for 8 hours to obtain 1.5 g of an intended m-phenylenediamine compound DA-2 (the compound on the right end of the above scheme). The yield was 80% with respect to the 2,4,6-trimethylbenzotrifluoride.

The spectrum data of the obtained m-phenylenediamine compound. DA-2 is shown below.

$^{1}$H NMR (300 MHz, $CDCl_3$) δppm 3.63 (brs, 4H), 2.21 (q, J=2.7 Hz, 6H), 2.06 (s, 3H), $^{19}$F NMR (282 MHz, $CDCl_3$) δppm −51.00 (s, 6F)

Preparation of m-phenylenediamine Compound DA-3

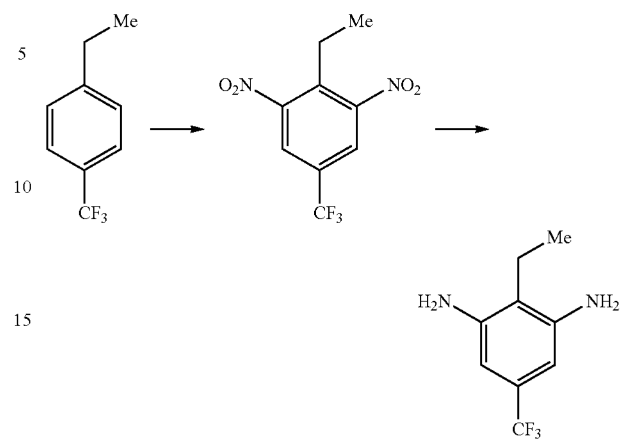

A m-phenylenediamine compound DA-3 was prepared as follows through the above scheme.

Into a three-necked flask, 25.0 g of 4-ethylbenzotrifluoride (manufactured by Manchester Organics Ltd.) was inserted, and cooled in an ice bath. After 250 mL of concentrated sulfuric acid (1.84 g/cm3, manufactured by FUJIFILM Wako Pure Chemical Corporation) was added thereto, 55 g of fuming nitric acid (1.52 g/cm3, manufactured by FUJIFILM Wako Pure Chemical Corporation) was carefully added dropwise thereto. The reaction was caused to proceed at an internal temperature of 40° C. for 5 hours, and the reaction product was then cooled with ice and carefully poured into ice. After filtration was carefully performed so that the target material was not dried, washing was performed with water and a saturated sodium bicarbonate solution to obtain 50 g of a dinitro compound including water.

Fifty grams of the dinitro compound was dissolved in 800 mL of methanol, and inserted into a 2 L autoclave. After 7.6 g of palladium-activated carbon (Pd 5%) (manufactured by FUJIFILM Wako Pure Chemical Corporation) was inserted and the autoclave was hermetically sealed, the autoclave was filled with hydrogen at about 5 MPa, and the reaction was caused to proceed at 40° C. for 6 hours. Filtration was carefully performed so that the palladium-activated carbon was not dried. The filtrate was concentrated under reduced pressure. Subsequently, the resulting solid was purified through silica gel columns using ethyl acetate and chloroform. The resulting crystal was vacuum-dried at 60° C. for 8 hours to obtain 24.0 g of an intended m-phenylenediamine compound DA-3 (the compound on the right end of the above scheme). The yield was 82% with respect to the 4-ethylbenzotrifluoride.

The spectrum data of the obtained m-phenylenediamine compound DA-3 is shown below.

$^{1}$H NMR (400 MHz, $CDCl_3$) δppm 6.39 (s, 2H), 3.72 (brs, 4H), 2.46 (q, J=8 Hz, 4H), 1.16 (t, J=8 Hz, 3H), $^{19}$F NMR (376 MHz, $CDCl_3$) δppm −63.03 (s, 6F)

The present invention has been described together with the embodiments thereof. However, we do not intend to limit our invention in any of the details of the description unless otherwise specified. We believe that the invention should be broadly construed without departing from the spirit and scope of the invention as defined by the appended claims.

REFERENCE SIGNS LIST

1 gas separation layer
2 porous layer

3 nonwoven fabric layer

10, 20 gas separation composite membrane

What is claimed is:

1. A polymer comprising a constituent component represented by formula (I) below, Formula (I)

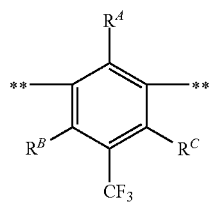

wherein in the formula (I), $R^A$, $R^B$, and $R^C$ represent a hydrogen atom, an alkyl group having 1 to 4 carbon atoms, or a halogen atom, at least one of $R^A$, $R^B$, or $R^C$ represents an alkyl group having 1 to 4 carbon atoms, the alkyl group having 1 to 4 carbon atoms is not trifluoromethyl,

** represents linking sites, and, the polymer is a polyimide compound or a polyamide compound.

2. The polymer according to claim 1, wherein the constituent component represented by the formula (I) is a component derived from a diamine.

3. A method for producing the polymer according to claim 1, the method comprising:

obtaining a polymer using a m-phenylenediamine compound represented by formula (Ia) below as a raw material, Formula (Ia)

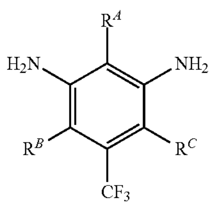

wherein in the formula (Ia), $R^A$, $R^B$, and $R^C$ have the same meaning as $R^A$, $R^B$, and $R^C$ in the formula (I), respectively.

4. A gas separation membrane comprising a gas separation layer including the polymer according to claim 1.

5. A gas separation membrane comprising, as a polymer for a gas separation layer, a polyimide compound having a constitutional unit represented by formula (II) below, Formula (II)

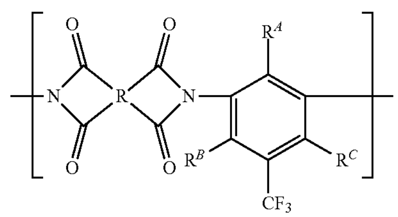

wherein in the formula (II), $R^A$, $R^B$, and $R^C$ represent a hydrogen atom, an alkyl group having 1 to 4 carbon atoms, or a halogen atom, at least one of $R^A$, $R^B$, or $R^C$ represents an alkyl group having 1 to 4 carbon atoms, the alkyl group having 1 to 4 carbon atoms is not trifluoromethyl, and R represents a group represented by any one of formulae (I-1) to (I-28) below, where $X^1$ to $X^3$ represent a single bond or a divalent linking group, L represents —CH═CH— or —$CH_2$—, $R^1$ and $R^2$ represent a hydrogen atom or a substituent, and * represents bonding sites with carbonyl groups in the formula (II).

(I-1)

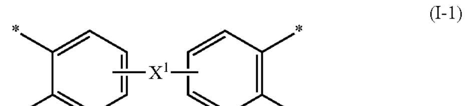

(I-2)

(I-3)

(I-4)

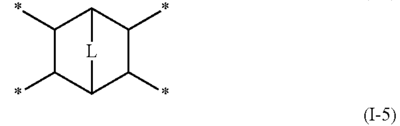

(I-5)

(I-6)

(I-7)

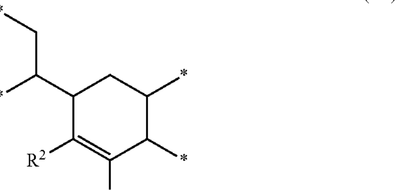

(I-8)

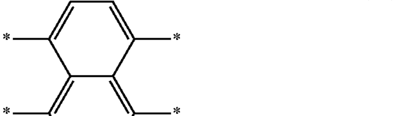

(I-9)

-continued

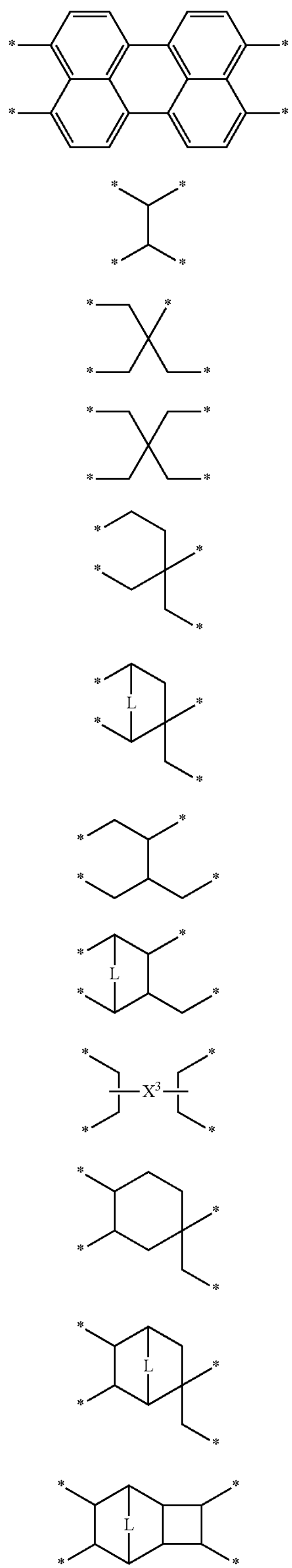

-continued

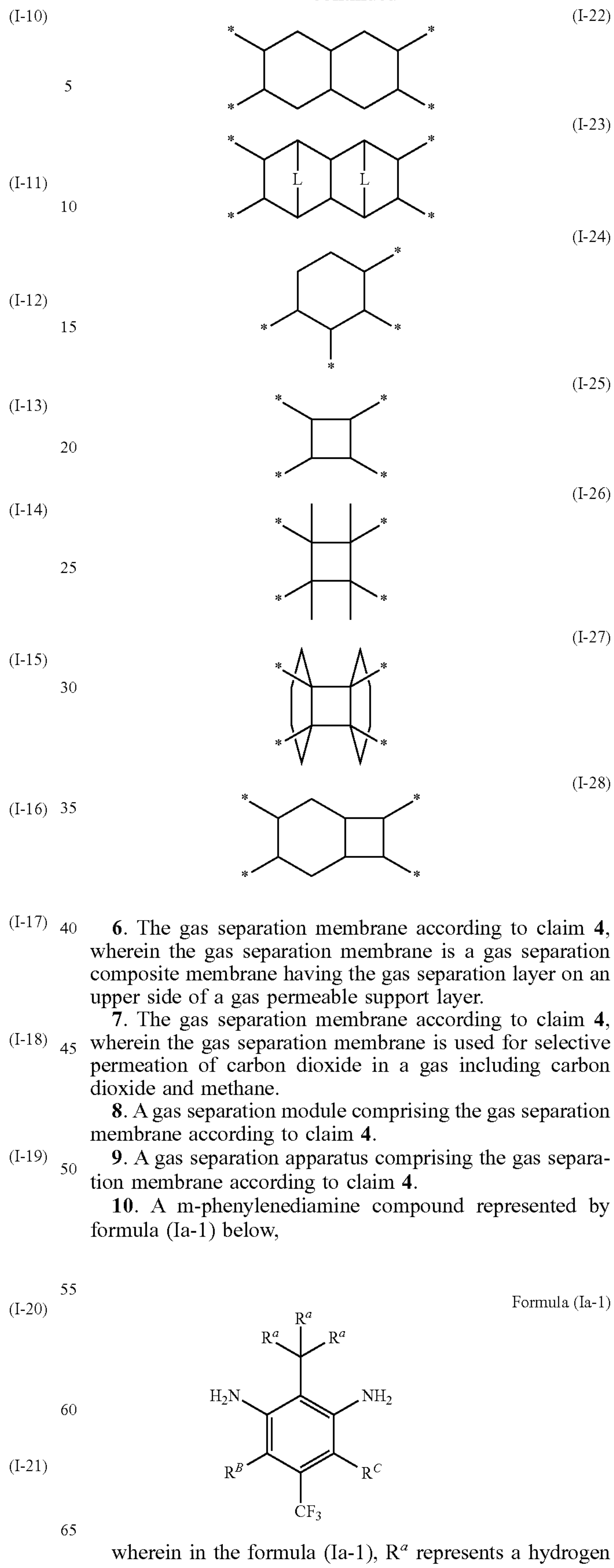

6. The gas separation membrane according to claim 4, wherein the gas separation membrane is a gas separation composite membrane having the gas separation layer on an upper side of a gas permeable support layer.

7. The gas separation membrane according to claim 4, wherein the gas separation membrane is used for selective permeation of carbon dioxide in a gas including carbon dioxide and methane.

8. A gas separation module comprising the gas separation membrane according to claim 4.

9. A gas separation apparatus comprising the gas separation membrane according to claim 4.

10. A m-phenylenediamine compound represented by formula (Ia-1) below,

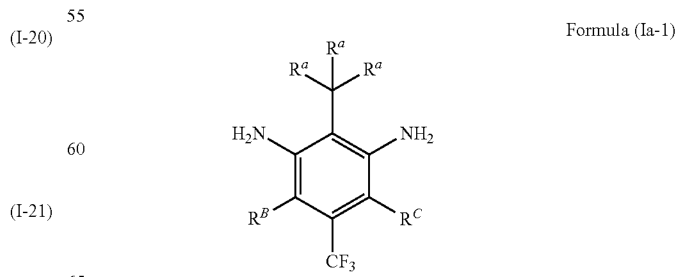

wherein in the formula (Ia-1), $R^a$ represents a hydrogen atom, an alkyl group having 1 to 3 carbon atoms, a halogen atom, a hydroxy group, an alkoxy group having 1 to 3 carbon atoms, or an acyloxy group having 1 to 3 carbon atoms, —$C(R^a)_3$ has 1 to 4 carbon atoms and is not trifluoromethyl, $R^B$ and $R^C$ represent a hydrogen atom, an alkyl group having 1 to 4 carbon atoms, or a halogen atom, the alkyl group that is represented by $R^B$ and $R^C$ and has 1 to 4 carbon atoms is not trifluoromethyl, and $R^B$, $R^C$ and all $R^a$s do not represent a hydrogen atom simultaneously.

* * * * *